US010753928B2

(12) United States Patent
Shoji et al.

(10) Patent No.: US 10,753,928 B2
(45) Date of Patent: Aug. 25, 2020

(54) PROTEIN DETECTION METHOD, AND PROTEIN IMMUNOASSAY METHOD

(71) Applicant: MORINAGA INSTITUTE OF BIOLOGICAL SCIENCE, INC., Yokohama-shi, Kanagawa (JP)

(72) Inventors: Masahiro Shoji, Yokohama (JP); Tsutomu Honjo, Yokohama (JP); Hideki Okada, Yokohama (JP); Kei Kurihara, Yokohama (JP)

(73) Assignee: Morinaga Institute of Biological Science, Inc., Kanagawa (JP)

( * ) Notice: Subject to any disclaimer, the term of this patent is extended or adjusted under 35 U.S.C. 154(b) by 141 days.

(21) Appl. No.: 16/062,496

(22) PCT Filed: Nov. 4, 2016

(86) PCT No.: PCT/JP2016/082875
§ 371 (c)(1),
(2) Date: Jun. 14, 2018

(87) PCT Pub. No.: WO2017/104289
PCT Pub. Date: Jun. 22, 2017

(65) Prior Publication Data
US 2018/0364219 A1    Dec. 20, 2018

(30) Foreign Application Priority Data
Dec. 14, 2015    (JP) .................................. 2015-243328
Sep. 20, 2016    (JP) .................................. 2016-183467

(51) Int. Cl.
| *G01N 33/53* | (2006.01) |
| *C07K 7/08* | (2006.01) |
| *C07K 16/18* | (2006.01) |
| *G01N 33/68* | (2006.01) |
| *G01N 33/02* | (2006.01) |

(52) U.S. Cl.
CPC ........... *G01N 33/5308* (2013.01); *C07K 7/08* (2013.01); *C07K 16/18* (2013.01); *G01N 33/02* (2013.01); *G01N 33/53* (2013.01); *G01N 33/6848* (2013.01); *G01N 33/6857* (2013.01); *C07K 2317/34* (2013.01)

(58) Field of Classification Search
None
See application file for complete search history.

(56) References Cited

U.S. PATENT DOCUMENTS 6,863,790 B1 * 3/2005 Moini .................... H01J 49/167
204/452

FOREIGN PATENT DOCUMENTS

| JP | 6-058935 | | 3/1994 |
| JP | 1999-140098 | A | 5/1999 |
| JP | 2000-186100 | A | 7/2000 |
| JP | 2004-239885 | A | 8/2004 |
| JP | 2005-106629 | A | 4/2005 |
| JP | 2007-525645 | A | 9/2007 |
| JP | 2008-175814 | | 7/2008 |
| JP | 2009-139107 | A | 6/2009 |
| JP | 2009-271092 | A | 11/2009 |
| JP | 2010-066225 | A | 3/2010 |
| JP | 2010-078455 | A | 4/2010 |
| JP | 2012-207954 | A | 10/2012 |
| JP | 2014-525588 | A | 9/2014 |
| WO | 2008/120684 | | 10/2008 |
| WO | 2010/095469 | | 8/2010 |
| WO | 2012/111249 | | 8/2012 |
| WO | 2016/156545 | | 3/2016 |

OTHER PUBLICATIONS

JP 2010-66225 Machine English Translation.*
JP 2005-106629 Machine English Translation.*
Trenchevska, et al., "Quantitatve mass spectrometric immunoassay for the chemokine RANTES and its variants", Journal of Proteomics, vol. 116, 2014, pp. 15-23.
Niederkofler, et al., "Targeted Selected Reaction Monitoring Mass Spectrometric Immunoassay for Insulin-like Growth Factor 1", PLOS ONE, vol. 8, No. 11, 2013, e81125 (6 pages).
Losito, et al., "Development of a Method for Quantification of Caseinate Traces in Italian Commercial White Wines Based on Liquid Chromatography—Electrospray Ionization—Ion Trap—Mass Spectrometry", Journal of Agricultural and Food Chemistry, vol. 61, 2013, pp. 12436-12444.
Monaci, et al., "Multi-allergen quantification of fining-related egg and milk proteins in white wines by high-resolution mass spectrometry", Rapid Communications in Mass Spectrometry, vol. 27, 2013, pp. 2009-2018.
International Search Report and Written Opinion; International Patent Application No. PCT/JP2016/082875, dated Feb. 7, 2017, with English translation (26 pages).
Yoshino et al., "Mass Spectrometry-Based Protein Identification by Correlation with Sequence Database", J. Mass Spectrom. Soc. Jpn. vol. 52., No. 3, pp. 106-129 (2004).
Marcon et al., "Assessment of a method to characterize antibody selectivity and specificity for use in immunoprecipitation", Nature Methods vol. 12, No. 8, pp. 725-731 (2015).

* cited by examiner

*Primary Examiner* — Changhwa J Cheu
(74) *Attorney, Agent, or Firm* — Hamre, Schumann, Mueller & Larson, P.C.

(57) ABSTRACT

Provided is a method for detecting a specific protein, having excellent reliability.
The method is characterized by including a mass spectrometry step of detecting the specific protein by mass spectrometry and an immunoassay step of detecting the specific protein by immunoassay using an anti-peptide antibody specifically bonded to the specific protein.

18 Claims, 6 Drawing Sheets
Specification includes a Sequence Listing.

FULL-LENGTH PROTEIN

ANTIGEN PEPTIDE

MASS SPECTROMETRY TARGET PEPTIDE FRAGMENTE

FULL-LENGTH PROTEIN

ANTIGEN PEPTIDE

MASS SPECTROMETRY TARGET PEPTIDE FRAGMENTE

EPITOPE

FULL-LENGTH PROTEIN

ANTIGEN PEPTIDE

MASS SPECTROMETRY TARGET PEPTIDE FRAGMENTE

EPITOPE

FULL-LENGTH PROTEIN

ANTIGEN PEPTIDE

MASS SPECTROMETRY TARGET PEPTIDE FRAGMENTE

EPITOPE

VERTICAL AXIS: RELATIVE INTENSITY WHEN STRONGEST SIGNAL INTENSITY ([M+2H]$^{2+}$) IS ASSUMED TO BE 100%
HORIZONTAL AXIS: m/z

VERTICAL AXIS: RELATIVE INTENSITY WHEN STRONGEST SIGNAL INTENSITY (QTALVLLK) IS ASSUMED TO BE 100%
HORIZONTAL AXIS: RETENTION TIME (MINUTE)

PROTEIN DETECTION METHOD, AND PROTEIN IMMUNOASSAY METHOD

TECHNICAL FIELD

The present invention relates to a method for detecting a protein in a sample, including an immunoassay step and a mass spectrometry step.

The present invention also relates to immunoassay for detecting a specific protein in a proteome, a method for producing an anti-peptide antibody used in the immunoassay method, and a method for designing an antigen peptide for producing the anti-peptide antibody.

BACKGROUND ART

Food allergy may induce a harmful immune response such as dermatitis, asthma, or anaphylactic shock, and has a risk leading to a fatal accident. In fact, it has been reported that about 150 people die from food allergy per year in the United States. In view of such a situation, many techniques for detecting an allergen in food have been proposed.

Currently, immunoassay using an antibody is generally used as a method for detecting an allergen. For example, Patent Literature 1 discloses a method for detecting a buckwheat allergen by ELISA or immunochromatography.

Meanwhile, a method for detecting an allergen in a sample using a mass spectrometer has been proposed. Patent Literature 2 discloses a method for detecting an allergen by liquid chromatography tandem mass spectrometry (LC-MS/MS).

Patent Literature 3 discloses a method for quantifying a specific protein contained in a sample by performing mass spectrometry by mixing a stable isotope-labeled protein with a sample, quantifying a plurality of peptide fragments based on a signal area ratio and a signal intensity ratio between a target protein-derived peptide fragment and a stable isotope-labeled protein-derived peptide fragment, and calculating an average value of the quantitative values of the peptide fragments.

By the way, a proteome is a collection of proteins existing in a biological system such as a cell, a tissue, or an organism. Comparing proteomes in a plurality of systems makes it possible to comprehensively understand a life phenomenon. A method for approaching a life phenomenon by comprehensively analyzing a proteome is referred to as proteomics.

In recent years, with development of mass spectrometry, it has become possible to accurately measure the mass of a small amount of protein fragments, and a method combining mass spectrometry with proteomics has been developed. Specifically, it has become possible to separate a protein contained in a proteome by electrophoresis, chromatography, or the like, to specify a protein having a difference in expression in a plurality of biological systems, to fragment the protein and measure the mass of the fragmented protein, and to identify the protein by comparing the obtained data with amino acid sequence data of a protein presumed from genome analysis.

As described above, with development of mass spectrometry, a proteomics technique has advanced dramatically, and has been actively performed not only in a basic research field of life science but also in a field of medical science searching for a causal protein of a human disease such as cancer (for example, Patent Literature 4).

After a specific protein is identified by mass spectrometry, it is required to detect the protein in a proteome for functional analysis of the protein. Therefore, a method for qualitatively or quantitatively detecting a specific protein in a proteome has been desired.

Under such a situation, as a method for quantifying a specific protein in a proteome, a method for performing relative quantification based on a peak intensity ratio in mass spectrometry while a stable isotope is used and one sample is used as an internal standard, has been proposed (Non-Patent Literature 1).

In addition, an ICAT method using chemical modification on a cysteine residue as a label instead of an isotope has been proposed (Non-Patent Literature 1).

By the way, immunoassay for performing an antigen-antibody reaction in the presence of an ionic surfactant is known (for example, Patent Literatures 5 and 6). In this method, a protein denatured by an ionic surfactant is detected.

CITATION LIST

Patent Literature

Patent Literature 1: JP 2009-271092 A
Patent Literature 2: JP 2014-525588 A
Patent Literature 3: WO 2012111249 A1 pamphlet
Patent Literature 4: JP 2010-078455 A
Patent Literature 5: JP 2004-239885 A
Patent Literature 6: JP 2005-106629 A

Non-Patent Literature

Non-Patent Literature 1: J. Mass Spectrom. Soc. Jpn. Vol. 52. No. 3, 106-129. 2004
Non-Patent Literature 2: Nature Methods 12, 725-731 (2015)

SUMMARY OF INVENTION

Technical Problem

An immunoassay test reagent generally used for detecting an allergen can be used in a simple and easy manner. Meanwhile, for example, an "egg" allergen test reagent causes the difference in measured values depending on the measuring objective protein such as ovalbumin, ovomucoid, and egg white lysozyme. Furthermore, even test reagents using the same ovalbumin protein as a detection target cause a difference in measured values depending on a measuring antibody reagent because an antigen determining site (epitope) of ovalbumin recognized by an antibody of one test reagent is different from that recognized by an antibody of another test reagent. This indicates difficulty of standardization using a standard in immunoassay. Furthermore, there is a problem in terms of reliability, such as occurrence of false positive due to a cross reaction, a prozone phenomenon, or the like, or insufficient quantitativeness in a low concentration region.

Meanwhile, mass spectrometry has advantages that standardization is easy because an object to be measured is obvious, quantitativeness is excellent because mass spectrometry has high specificity and sensitivity, and simultaneous measurement of multiple items is possible. However, efficiency of ionization of a peptide fragment varies depending on each peptide fragment. In order to quantify a protein by mass spectrometry, it is very important to select a target peptide fragment which is included in the protein sequence, and various criteria to choose the target fragment are being studied, but selection of a peptide fragment to be quantified is a difficult step at present.

In addition, there is a problem, for example, an error in a process of a target protein fragmentation in a sample, that is, digestion efficiency of fragmentation and sample loss due to adsorption of the target protein on a tube etc. are hardly corrected.

As a means for solving the above problem, a method described in Patent Literature 3 has been proposed. However, there is a problem that a protein labeled with a stable isotope, which is used as an internal standard, needs to be prepared.

In addition, there are significant disadvantages as an analytical technique, for example, huge initial investment due to a very expensive mass spectrometer, a high level of expertise required for operation, maintenance, and management of the device, a tedious enzyme digestion to obtain a peptide fragment, and a carefulness for the suppression of target ionization all the time. In addition, unlike immunoassay, a measurement system is not provided to the market in a state optimized for a specific detection target. Therefore, at present, an in-house technique that adjusts a measurement system for own purpose by combining optimal conditions for each item is required.

In view of such a situation, a first problem to be solved by the present invention is to provide a method for detecting a specific protein with excellent reliability. In addition, in a preferable embodiment of the present invention, an object is to provide a method for detecting a specific protein having excellent economic benefit.

As for a method for performing relative quantification of a specific protein in a proteome using a stable isotope as described in Non-Patent Literature 1, there is a disadvantage that a general search engine cannot be used because an isotope-labeled protein has a molecular weight different from an original molecular weight.

As for the ICAT method, biotin as a labeler makes fragmentation of a protein complicated, and therefore there is a problem that an unidentified spectrum data that cannot be attributed by mass spectrometry is generated.

Furthermore, as for these methods for quantifying a specific protein by mass spectrometry, it is tedious to perform a pretreatment such as reductive alkylation or enzyme digestion, and there is also a problem that it takes significant time for the sample treatment of many samples, which is specific to mass spectrometry.

Under such a situation, development of a novel technique for measuring a specific protein in a proteome has been desired.

Meanwhile, an immunological method is widely used as a method for detecting a protein qualitatively or quantitatively. The immunological method is a simple method, and has high specificity, therefore is useful for detecting a specific protein, which is identified from a proteome by mass spectrometry.

However, an anti-protein antibody normally has a property of recognizing a surface of a folded antigen protein structure, that is, bonding to a three-dimensional structure of the antigen protein. Meanwhile, mass spectrometry is a method for detecting a peptide fragment, that is, a primary structure of a protein. As described above, immunoassay using an anti-protein antibody and mass spectrometry have different detection targets. Therefore, there is a problem that measurement results by both measurement methods do not necessarily correlate with each other.

Accordingly, it is necessary to perform a complicated conformational test in order to ensure if the protein showing the reactivity to an anti-protein antibody, excluding the possibility like the false positive result due to a cross reaction, is the one identified by mass spectrometry. Examples of such a conformational test include a test using a culture cell lacking a gene of the identified protein or a test using a recombinant protein of the identified protein.

In addition, a protein newly identified in proteomics has not been studied in detail in many cases. Therefore, it is rare that such protein is commercially available. Therefore, it is necessary to purify the protein from a cell, a tissue, or the like, or to produce a recombinant protein newly and produce an antibody using the recombinant protein as an antigen.

As described above, there is a problem that it takes much time, cost, and labor to produce an anti-protein antibody against a protein newly identified in proteomics.

In view of such a situation, a second issue to be solved by the present invention is to provide a technique capable of performing immunoassay that can afford a result highly correlated with mass spectrometry.

Solution to Problem

The present invention for solving the first issue is a method for detecting a specific protein in a sample, including:

a mass spectrometry step of detecting the specific protein by mass spectrometry; and an immunoassay step of detecting the specific protein by immunoassay using an anti-peptide antibody specifically bonded to the specific protein.

A preferable embodiment of the present invention is characterized in that an amino acid sequence constituting a partial peptide of the specific protein, which is used as an antigen for producing the anti-peptide antibody, and an amino acid sequence constituting a peptide fragment detected in the mass spectrometry step have the identical sequence containing at least four amino acid residues.

In the method according to such an embodiment of the present invention, a peptide containing the identical amino acid sequence is detected in the immunoassay step and the mass spectrometry step, thus results obtained by both analytical steps have high correlation with each other. Consequently, according to the method of the present invention, both measurement results can be obtained with high reliability.

A preferable embodiment of the present invention is characterized in that an amino acid sequence constituting a partial peptide of the specific protein, which is used as an antigen for producing the anti-peptide antibody, and an amino acid sequence constituting a peptide fragment corresponding to a signal detected with an intensity of 50% or more of a signal detected as the highest intensity in mass spectrometry analysis of a peptide solution obtained by treating the specific protein with a proteolytic enzyme has the identical sequence containing at least four amino acid residues with the sequence constituting a partial peptide of the specific protein used for producing the anti-peptide antibody.

According to such an embodiment, a measurement result with high reliability can be obtained.

In a preferable embodiment of the present invention, the peptide fragment has the identical amino acid sequence as at least a part of an amino acid sequence specifically recognized by the anti-peptide antibody.

According to such an embodiment, it is possible to improve the correlation between a result obtained by the immunoassay step and that obtained by the mass spectrometry step, and to accomplish higher reliability of a measurement result.

In a preferable embodiment of the present invention, the immunoassay is a method performing its antigen-antibody reaction in the presence of an ionic surfactant.

When a protein is placed in the presence of an ionic surfactant, a folded protein structure is unfolded, and an anti-peptide antibody can be bonded to an amino acid sequence, which is normally folded inside, accordingly it is hardly accessible by the antibody.

A preferable embodiment of the present invention includes a quantitation step calculating a quantitative value of the content of a specific protein in a sample by comparing a result obtained in the immunoassay step with that obtained in the mass spectrometry step.

By comparing the detection result obtained in the immunoassay step with that obtained in the mass spectrometry step, a quantitative value can be quantified with higher reliability.

A preferable embodiment of the present invention includes an extraction step of treating a sample with an ionic surfactant to obtain a protein solution. In the immunoassay step, a specific protein contained in the protein solution is detected. In the mass spectrometry step, a peptide fragment containing the specific amino acid sequence is detected using a peptide solution obtained by treating a protein solution with a proteolytic enzyme.

In such an embodiment, a protein solution obtained in the same extraction step can be analyzed both in the immunoassay step and the mass spectrometry step, and therefore a measurement result can present higher reliability.

In a preferable embodiment of the present invention, a solution containing a standard peptide, which is a partial peptide of the specific protein, contains at least a part of an amino acid sequence constituting the peptide fragment detected in the mass spectrometry step, and to which the anti-peptide antibody can be bonded, is used as a standard solution.

By using such a solution containing a standard peptide as analytical standard, the reliability of a quantitative value obtained by the method of the present invention can be improved.

In a more preferable embodiment of the present invention, the standard solution used in the immunoassay step and the standard solution used in the mass spectrometry step include the same standard peptide.

As described above, by measuring the common standard peptide in the immunoassay step and the mass spectrometry step, the standardization between different measurement methods i.e. immunoassay and mass spectrometry analysis, is achievable.

In the present invention, in a case where a result of the immunoassay step is positive, the mass spectrometry step may be performed successively.

Such an embodiment is preferable in order to eliminate false positive of the immunoassay step or to accurately quantify the amount of a target protein contained in an immunoassay-positive sample.

In addition, in the present invention, in a case where it is difficult to determine whether a result of the immunoassay step is positive or negative, the mass spectrometry step may be performed complementary.

In a case where there is no necessity of accurate quantification of a specific protein in a sample that has been clearly positively determined in the immunoassay step or in a case where accurate determination of positive or negative is required, such an embodiment is preferable.

In addition, in the present invention, in a case where a result of the immunoassay step is negative, the mass spectrometry step may be performed.

In a case where it is intended to detect a target protein although the content of the target protein is equal or less than the detection limit of the immunoassay, or intended to exclude false negative by the immunoassay, such an embodiment is preferable.

In addition, in a preferable embodiment of the present invention, in the mass spectrometry step, an ion derived from the peptide fragment can be selectively detected.

By making the mass spectrometry step to an ion selective detection form, noise of mass spectrometry can be eliminated, and a more accurate quantitative result can be obtained.

In a preferable embodiment of the present invention, the peptide fragment corresponds to a signal detected with an intensity of 50% or more of a signal detected as the highest intensity by mass spectrometry analysis using a peptide solution obtained by treating the protein with a proteolytic enzyme.

In such an embodiment of the invention, the immunoassay step is performed with an anti-peptide antibody that recognizes an amino acid sequence contained in a peptide fragment that can be detected by mass spectrometry. Therefore, it is possible to confirm a result of the immunoassay step with better accuracy.

The method of the present invention is suitable for testing a food sample.

In addition, the present invention is preferably applied for detecting a food allergen.

In addition, the present invention also relates to a method for screening a sample subjected to mass spectrometry for detecting a protein, characterized to include an immunoassay step detecting the protein in the sample by immunoassay using an anti-peptide antibody recognizing a specific amino acid sequence contained in the target protein.

By the screening step of the present invention, it is possible to reduce cost and labor for the mass spectrometry step and to improve economic efficiency.

In addition, the present invention for solving the mentioned second issue is an immunoassay detecting a specific protein in a proteome, characterized to include the following steps.

(1) A separation step to separate a protein in a sample (2) A mass spectrometry step to identify the separated protein of the separation step by mass spectrometry (3) An immunoassay step to measure the separated protein of the separation step in the sample, by the immunoassay using an anti-peptide antibody specifically bonded to the separated protein A peptide fragment, that is, a primary structure of a protein is the detection target in the mass spectrometry analysis. Meanwhile, an anti-peptide antibody used in the immunoassay similarly recognizes a primary structure of a protein. As described above, the detection targets of both mass spectrometry and immunoassay are the same. Therefore, the immunoassay of the present invention can accomplish highly correlated result with that by mass spectrometry.

A preferable embodiment of the present invention includes the following steps for producing the anti-peptide antibody after the mass spectrometry step.

(A) A selection step to choose the amino acid sequence containing four or more amino acid residues presenting high specificity in the whole amino acid sequences constituting in a separated protein of the separation step (B) A peptide synthesis step to synthesize the partial peptide containing an amino acid sequence selected by the selection step (C) An antibody production step to produce the anti-peptide antibody using the partial peptide as an antigen A measurement result obtained by the immunoassay according to the present invention has higher correlation with the result of mass spectrometry. Namely, according to such an embodiment, it is possible to obtain a reliable measurement result that excludes false positive due to a cross reaction, and has a high possibility to measure the same protein identified by mass spectrometry.

In addition, by the steps (A) to (C), an antibody capable of specifically detecting a specific protein in a proteome identified by mass spectrometry can be produced with minimizing time, cost, and labor.

In a preferable embodiment of the present invention, the mass spectrometry step is performed analyzing a peptide solution obtained by the proteolytic enzyme treatment of the protein separated in the separation step, and the anti-peptide antibody using the antigen, which is a partial peptide of the protein separated in the separation step, and is the partial peptide having at least four amino acid residues as those of the amino acid sequence constituting one or more peptide fragments corresponding to a signal detected with an intensity of 50% or more of a signal detected as the highest intensity by the mass spectrometry, is used in the immunoassay step.

By using such anti-peptide antibody, an immunoassay result can present the excellent correlation with that of mass spectrometry.

In a preferable embodiment of the present invention, the separation step is performed by two-dimensional electrophoresis. The two-dimensional electrophoresis is excellent as a protein separation method.

The present invention also relates to a method for designing an antigen peptide for producing an anti-peptide antibody used for detecting an antigen protein by immunoassay.

That is, the present invention relates to a method for designing an antigen peptide characterized that a partial peptide of the antigen protein satisfying at least four amino acid residues are same as those of an amino acid sequence in one or more peptide fragments detected by mass spectrometry of the peptide solution obtained by treating an antigen protein with a proteolytic enzyme is used as a first antigen candidate.

According to the designing method of the present invention, it is possible to design an antigen peptide for producing an anti-peptide antibody capable to make immunoassay result high correlate with that of mass spectrometry.

In a preferable embodiment of the present invention, the peptide fragment is one or more peptide fragments corresponding to a signal with an intensity of 50% or more of a signal as the highest intensity detected by the mass spectrometry.

According to such an embodiment, it is possible to easily design an antigen peptide of an anti-peptide antibody that can recognize a part of an amino acid sequence constituting a peptide fragment that can be detected with high sensitivity in the mass spectrometry step.

In addition, according to such an embodiment, it is possible to design an antigen peptide for producing an anti-peptide antibody capable of realizing immunoassay that can achieve higher correlation with mass spectrometry.

It is useful to apply the designing method of the present invention to design an anti-peptide antibody used in immunoassays that performs an antigen-antibody reaction in the presence of an ionic surfactant.

In the presence of an ionic surfactant, a protein is denatured, and an amino acid sequence normally located inside as a folded structure is also exposed to outside. Therefore, it is unnecessary to consider for a three-dimensional structure of a protein when designing an antigen peptide.

In a preferable embodiment of the present invention, a partial peptide containing an amino acid sequence having higher specificity among the first antigen candidates is used as a secondary antigen candidate.

According to such an embodiment, it is possible to design an antigen peptide capable of producing a highly specific anti-peptide antibody.

It is useful to apply the designing method of the present invention to production of an anti-peptide antibody used for detecting a protein identified by mass spectrometry.

In addition, it is useful to apply the designing method of the present invention to produce an anti-peptide antibody used for detecting a specific protein identified in proteomics.

Furthermore, it is useful to apply the designing method of the present invention to production of an anti-peptide antibody used in the above-described immunoassay.

The present invention also relates to a method for producing an anti-peptide antibody used for detecting an antigen protein by immunoassay.

That is, the present invention relates to a method for producing an anti-peptide antibody characterized that a partial peptide of the antigen protein satisfying at least four amino acid residues are the same as those of an amino acid sequence in one or more peptide fragments detected by mass spectrometry of the peptide solution obtained by treating an antigen protein with a proteolytic enzyme is used as an antigen.

According to the present invention, it is possible to produce an anti-peptide antibody capable to establish the immunoassay highly correlated with mass spectrometry.

In a preferable embodiment of the present invention, the peptide fragment corresponds to a signal detected with an intensity of 50% or more of a signal detected as the highest intensity by the mass spectrometry.

According to such an embodiment, it is possible to produce an anti-peptide antibody capable to establish the immunoassay having highly correlated with mass spectrometry.

It is useful to apply the present invention to produce an anti-peptide antibody used in the immunoassay where an antigen-antibody reaction is performed in the presence of an ionic surfactant.

In a preferable embodiment of the present invention, the partial peptide contains an amino acid sequence with high specificity in the whole amino acid sequences constituting an antigen protein.

According to such an embodiment, an anti-peptide antibody with high specificity can be produced.

Advantageous Effects of Invention

According to the present invention, it is possible to provide a technique for detecting a specific protein with high reliability. In addition, according to a preferable embodiment of the present invention, it is possible to provide a method for detecting a specific protein having excellent economic benefit.

In addition, according to the immunoassay of the present invention, it is possible to obtain a result highly correlated with a result of mass spectrometry.

In addition, according to the production method and the designing method of the present invention, it is possible to produce an anti-peptide antibody capable of performing immunoassay highly correlated with mass spectrometry, and to design an antigen peptide for producing the anti-peptide antibody.

In addition, by using an anti-peptide antibody provided by the production method and the designing method of the present invention, it is possible to obtain a result correlated with mass spectrometry by simple and easy immunoassay, which does not need a complicated step requiring in mass spectrometry. Therefore, according to the present invention, it is possible to provide an anti-peptide antibody able to establish the immunoassay capable of measuring many samples at one time and suitable for routine management measurement, those are difficult by mass spectrometry.

DESCRIPTION OF EMBODIMENTS

<1> Method for Detecting Specific Protein in Sample (1) Detection Target

Figure 1:
FIG. 1 is a diagram schematically illustrating a full-length specific protein (upper row), an antigen peptide used for producing an anti-peptide antibody used in an immunoassay step (middle row), and a peptide fragment generated by digesting a specific protein with a proteolytic enzyme (lower row).
Figure 1:
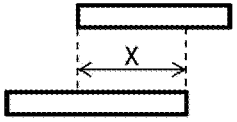

A detection target in the immunoassay step and the mass spectrometry step will be described with reference to FIGS. 1 to 4. FIG. 1 is a diagram schematically illustrating a full-length specific protein (upper row), an antigen peptide used for producing an anti-peptide antibody used in an immunoassay step (middle row), and a peptide fragment that is generated by digesting a specific protein with a proteolytic enzyme and is a detection target in a mass spectrometry step (hereinafter also referred to as a mass spectrometry target peptide fragment) (lower row).

The present invention is characterized in that a mass spectrometry target peptide fragment has the same amino acid sequence as a part of an amino acid sequence constituting an antigen peptide of an anti-peptide antibody used in an immunoassay step (FIG. 1).

With this characteristic, a measurement result in the immunoassay step and a measurement result in the mass spectrometry step have correlation with each other. Therefore, according to the method of the present invention, it is possible to obtain a detection result of a specific protein in a sample having high reliability.

In the present invention, the length of an amino acid sequence portion common to an antigen peptide and a mass spectrometry target peptide fragment, that is, the length of an amino acid sequence indicated by X in FIG. 1 (hereinafter also referred to as a common amino acid sequence) is preferably four or more amino acid residues, more preferably six or more amino acid residues, and still more preferably ten or more amino acid residues.

The length of the common amino acid sequence is preferably 10% or more, more preferably 20% or more, and still more preferably 30% or more, of the length of the antigen peptide.

By setting the peptide length of the common amino acid sequence within the above range, it is possible to obtain a detection result of a specific protein with high reliability.

Figure 2:
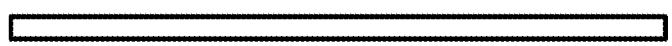
FIG. 2 is a diagram schematically illustrating a case where an epitope sequence of an anti-peptide antibody used in an immunoassay step deviates from a common amino acid sequence.
Figure 2:
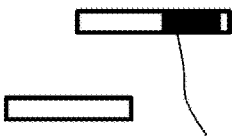

In the present invention, the length of the common amino acid sequence is preferably at least four amino acid residues. That is, an embodiment in which an amino acid sequence specifically recognized by an anti-peptide antibody used in the immunoassay step, that is, an epitope sequence deviates from the common amino acid sequence is also included in a technical scope of a preferable embodiment of the present invention (FIG. 2).

In the present invention, a part (FIG. 3) or the whole (FIG. 4) of an amino acid sequence constituting a mass spectrometry target peptide fragment preferably overlaps with the epitope sequence of the anti-peptide antibody.

(2) Immunoassay Step

In the immunoassay step, a specific protein is detected by immunoassay using an anti-peptide antibody.

The kind of immunoassay is not particularly limited, and examples thereof include immunoassay such as immunochromatography or ELISA using an anti-peptide antibody labeled with a labeling substance.

Specifically, it is possible to use known immunoassay such as a sandwich method using a labeled antibody (secondary antibody) that recognizes a specific protein after the specific protein is captured by an anti-peptide antibody bonded to an insoluble carrier, a sandwich method using a labeled anti-peptide antibody (secondary antibody) after a specific protein bonded to an insoluble carrier is captured by an antibody that recognizes the specific protein, or a competitive method for causing a specific protein in a sample to react with an anti-peptide antibody bonded to an insoluble carrier in the presence of a labelled antigen. Among these methods, a sandwich ELISA is preferable from a viewpoint of high sensitivity.

Specific examples of the labeling substance include an enzyme such as alkaline phosphatase or HRP, an antibody in an Fc region, and a fluorescent substance such as GFP.

Preferable examples of immunoassay include a method for performing an antigen-antibody reaction in the presence of an ionic surfactant. When a protein is placed in the presence of an ionic surfactant, a folded structure thereof is unraveled, and an anti-peptide antibody can be bonded also to an amino acid sequence normally folded inside.

A procedure of adding an ionic surfactant is not particularly limited. As described below, a protein may be extracted from a sample with an extraction solvent containing an ionic surfactant, and an antigen-antibody reaction may be performed without performing solvent replacement. In addition, an ionic surfactant may be added after a protein is extracted from a sample.

As the antibody used in the present invention, an anti-peptide antibody produced using a partial peptide of a specific protein as an antigen peptide is used. The anti-peptide antibody is not particularly limited as long as being an antibody that specifically recognizes an antigen peptide, and either a monoclonal antibody or a polyclonal antibody can be used.

As the anti-peptide antibody used in the immunoassay step, a commercially available anti-peptide antibody or a newly produced anti-peptide antibody may be used.

Here, examples of a method for producing an anti-peptide antibody include a method (i) for bonding an antigen peptide to a carrier protein such as albumin or keyhole limpet hemocyanin and immunizing an immune animal with the antigen peptide, and a method (ii) for immunizing an immune animal with a specific protein and purifying an antibody specifically bonded to an antigen peptide from an antiserum obtained from the immune animal using a column carrying the antigen peptide thereon.

Production of an anti-peptide antibody by the above method (i) can be performed according to a conventional method.

In a case where a polyclonal anti-peptide antibody is produced, first, an antigen (a specific protein or a partial peptide thereof) bonded to a carrier is well mixed with an adjuvant, and the resulting mixture is administered to an animal such as a rabbit, a goat, a rat, a mouse, a bird, or a horse to immunize the animal. After a lapse of a predetermined period of time from the immunization, the whole blood is collected to obtain an antiserum. This antiserum can be purified by salting out, column, or the like, and a polyclonal anti-peptide antibody can be obtained.

In a case where a monoclonal anti-peptide antibody is produced, first, an immune animal is immunized with an antigen peptide bonded to a carrier, and for example, a mouse spleen cell as a lymphocyte producing an antibody and a myeloma cell are fused with polyethylene glycol or the like to obtain a hybridoma. Among these cells, a cell that produces an antibody against an antigen peptide is screened and cultured, and an anti-peptide antibody can be thereby obtained.

Production of an anti-peptide antibody by the above method (ii) can be performed, for example, as follows.

An immune animal such as a mouse, a rat, a sheep, a goat, or a rabbit is immunized with a purified specific protein to obtain an antiserum.

More preferably, by subjecting the purified specific protein to a heat treatment, a treatment with an ionic surfactant such as SDS, or a treatment with both an ionic surfactant and a reducing agent such as 2-mercaptoethanol, dithiothreitol, or sodium sulfite, a denatured specific protein as an immunogen is obtained. An immune animal such as a mouse, a rat, a sheep, a goat, or a rabbit is immunized with the denatured specific protein thus obtained.

The antiserum thus obtained from an immune animal is purified using a purification column carrying an antigen peptide thereon.

Specifically, the antigen peptide is immobilized by a covalent bond on a resin for chromatography, for example, CNBr activated Sepharose or HiTrap NHS-activated (manufactured by Amersham Pharmacia), and the antiserum is provided to the immobilized resin. Then, a polyclonal antibody specifically bonded to an amino acid sequence constituting an antigen peptide contained in the antiserum is adsorbed on the resin, and then the polyclonal antibody adsorbed on the resin is eluted using an appropriate buffer, a chaotropic ion, or the like. As a result, an anti-peptide antibody specifically bonded to the antigen peptide can be obtained.

Before the purification, intermediate purification using a column carrying a denatured specific protein thereon may be performed.

Examples of an antigen peptide used in the methods (i) and (ii) include a chemically synthesized antigen peptide, an antigen peptide obtained by cleaving a specific protein with a proteolytic enzyme and purifying the resulting product, and an antigen peptide obtained by incorporating the whole or a part of cDNA encoding an amino acid sequence constituting an antigen peptide into a vector by a conventional method, transforming a host microorganism such as *Escherichia coli* or a cultured cell with this vector, and purifying a recombinant protein or a polypeptide obtained by culturing and producing the transformed host microorganism such as *Escherichia coli*/cultured cell with an affinity column, a nickel column, or the like.

The immunoassay step preferably includes an extraction step for extracting a specific protein from a sample. An extraction solvent used in the extraction step is not particularly limited but is preferably an aqueous solvent containing an ionic surfactant.

By using an aqueous solvent containing an ionic surfactant as an extraction solvent, even in a case where an epitope sequence of an anti-peptide antibody is buried inside a molecule in a specific protein maintaining a steric structure, the amino acid sequence can be exposed, and an antigen-antibody reaction between the specific protein and the anti-peptide antibody can occur.

Preferable examples of the aqueous solvent include pure water; a salt solution of sodium chloride, potassium chloride, or sodium bicarbonate; various buffers normally used in the biochemical field, such as a phosphate buffer, a tris-hydrochloric acid buffer, or a citrate buffer; and a solvent based on an alkaline solution having a pH adjusted with sodium hydroxide, hydrochloric, or the like, or an acidic solution.

The aqueous solvent may contain a chelate compound such as ethylenediamine tetraacetic acid (EDTA), an enzyme such as phospholipase, and a nonionic surfactant for HLB value control as an auxiliary component to additionally improve the solubility and extraction efficiency of a protein.

In addition, the aqueous solvent may contain a protease inhibitor for controlling decomposition of a protein in a solution during extraction or during storage, an antimicrobial substance for preventing propagation of a microorganism, such as sodium azide, or an antioxidant such as ascorbic acid.

Furthermore, the aqueous solvent may contain a polar organic solvent such as glycerol or ethanol as long as the aqueous solvent does not make an antigen-antibody reaction between a specific protein and an anti-peptide antibody impossible.

In addition, the aqueous solvent may contain a reducing agent typified by 2-mercaptoethanol, dithiothreitol (DTT), sodium cyanoborohydride (SCBH), dimethylamine borane (DMAB), sodium borohydride (SBH), sodium sulfite, or cysteine.

As the ionic surfactant contained in the aqueous solvent, any known ionic surfactant may be used as long as being able to substantially improve the solubility and extraction efficiency of a protein.

The ionic surfactant is suitably selected from the group consisting of sodium dodecyl sulfate, lithium dodecyl sulfate, sodium lauryl sarcosinate, hexadecyl trimethyl ammonium bromide, hexadecyl trimethyl ammonium chloride, hexadecyl pyridinium chloride, and mixtures thereof.

Sodium dodecyl sulfate (SDS) is a particularly suitable ionic surfactant.

The concentration of the ionic surfactant in the aqueous solvent may be any concentration as long as being able to achieve substantial solubilization and extraction of a specific protein, but is normally 0.1% (W/V) or more, and may be 0.3% (W/V) or more, 0.5% (W/V) or more, or about 10% (W/V).

In addition, the concentration of the ionic surfactant in the aqueous solvent is preferably 0.1 to 10% (W/V), more preferably 0.3 to 5% (W/V), and still more preferably 0.5 to 1% (W/V).

By setting the concentration of the ionic surfactant within the above range, it is possible to efficiently extract a specific protein from a sample and to improve efficiency of an antigen-antibody reaction.

In the extraction step, a protein solution can be obtained by extracting and/or solubilizing a specific protein in a sample by a known method.

Specifically, the protein solution can be obtained by treating an aqueous solvent containing a sample with a homogenizer, an ultrasonic crusher, a mortar, or the like, centrifuging the resultant suspension, and recovering the supernatant.

In the present invention, it is also preferable to heat an aqueous solvent containing a sample after the aqueous solvent is treated with a homogenizer, an ultrasonic crusher, a mortar, or the like. Extraction efficiency and dissolution efficiency of a specific protein can be improved by heating.

In a case where a sample is solid or semisolid, it is preferable to crush the sample with a mixer or the like in advance to obtain a minced product or a paste-like product from a viewpoint of extraction efficiency and dissolution efficiency of a specific protein.

In the immunoassay step, it is preferable to bring a protein solution obtained in the extraction step into contact with an anti-peptide antibody without substantially diluting the protein solution.

Alternatively, it is preferable to bring a protein solution diluted in a range where the concentration of an ionic surfactant does not become 0.03% (W/V) or less into contact with an anti-peptide antibody.

Here, the form of "bringing a protein solution into contact with an anti-peptide antibody" is not limited as long as being able to cause an antigen-antibody reaction between the specific protein in a protein solution and the anti-peptide antibody.

In a case where the immunoassay step is performed by a sandwich method or a competitive method, an antigen-antibody complex can be formed by bringing a protein solution into contact with an immobilized anti-peptide antibody.

In addition, an antigen-antibody complex can also be formed by bringing an anti-peptide antibody into contact with an antigen protein captured by an immobilized anti-protein antibody.

Preferable examples of such a method include a latex aggregation method and an ELISA method.

(3) Mass Spectrometry Step

The mass spectrometry step detects a peptide fragment (mass spectrometry target peptide fragment) that is a partial peptide of a specific protein and has an amino acid sequence in which at least four amino acid residues are the same as those of an amino acid sequence constituting an antigen peptide.

A mass spectrometer used in the mass spectrometry step is not particularly limited as long as being able to detect a mass spectrometry target peptide fragment.

Specifically, it is possible to use LC-MC, GC-MS, and CE-MS having sample introduction parts thereof directly connected to high performance liquid chromatography (HPLC), gas chromatograph (GC), and capillary electrophoresis (CE), respectively. In particular, in a case where a sample to be analyzed is a food sample, LC-MS is preferably used.

In addition, as an ion source, it is also possible to use a mass spectrometer adopting any ionization method such as an electron ionization (EI) method, a chemical ionization (CI) method, a field desorption (FD) method, a fast atom bombardment (FAB) method, a matrix assisted laser desorption ionization (MALDI) method, an electrospray ionization (ESI) method, an atmospheric pressure chemical ionization (APCI) method, inductively coupled plasma (ICP), a DART method using Penning ionization, or an ion attachment method (IA) for attaching a lithium ion to a gas phase sample.

As an analysis unit which is a site for separating an ionized sample, it is also possible to use a mass spectrometer adopting any analysis unit such as a magnetic sector type, a quadrupole type (Q), an ion trap type (IT), a time-of-flight type (TOF), a Fourier-transform ion cyclotron resonance type (FT-ICR), an accelerator mass spectrometry (AMS), or a tandem type combining a plurality of the above analysis methods.

In the mass spectrometry step of the present invention, a mass spectrometry target peptide fragment may be selectively detected.

Specifically, adjustment may be performed such that a mass spectrometer having a quadrupole type analysis unit causes only one charged particle (one mass charge ratio) derived from a mass spectrometry target peptide fragment to pass through a detector by selected ion monitoring (SIM).

In addition, using MS/MS combining two quadrupole type analysis units as a mass spectrometer, only an ion derived from a mass spectrometry target peptide fragment can be selectively detected by multiple reaction monitoring (MRM).

By selectively detecting only a mass spectrometry target peptide fragment in this way, another peptide fragment in a sample is not detected at all, and all the ions derived from the mass spectrometry target peptide fragment having a specific m/z can be detected. Therefore, noise can be reduced, and sensitivity can be largely improved.

In the present invention, in a case where mass spectrometry is performed using a peptide solution obtained by treating a specific protein with a proteolytic enzyme as a sample, it is preferable to use a peptide fragment corresponding to a signal detected with an intensity preferably of 50% or more, more preferably of 70% or more, still more preferably of 90% or more, further still more preferably of 100%, of a signal detected with the highest intensity, as a mass spectrometry target peptide fragment.

In such an embodiment, the immunoassay step is performed with an anti-peptide antibody that specifically recognizes an antigen peptide having the same amino acid sequence as a peptide fragment that can be detected with good sensitivity in the mass spectrometry step.

Therefore, according to such an embodiment of the present invention, a specific protein in a sample can be detected with higher accuracy.

(4) Embodiment of Method of the Present Invention

Hereinafter, an embodiment of the present invention will be further described.

As described above, it is preferable to treat a sample with an ionic surfactant to obtain a protein solution containing a specific protein, and to detect the specific protein contained in the protein solution in the immunoassay step.

Figure 5:
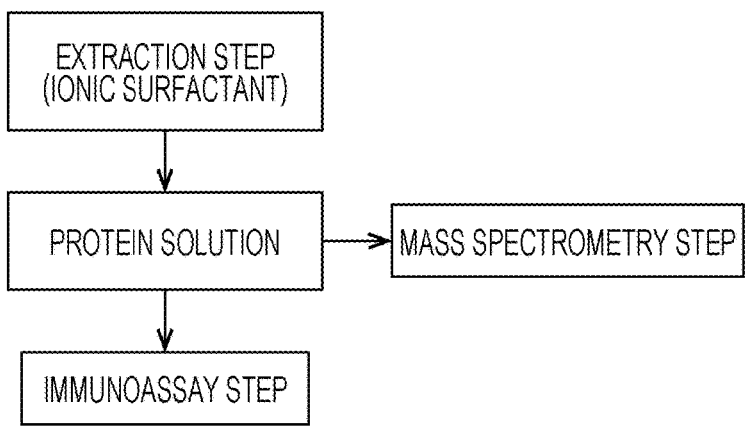
FIG. 5 is a diagram schematically illustrating an embodiment of providing a protein solution containing a specific protein obtained by treating a sample with an ionic surfactant as a sample in an immunoassay step and providing a peptide solution obtained by treating a protein solution or a treated product thereof with a proteolytic enzyme as a sample in a mass spectrometry step.

In a more preferable embodiment of the present invention, the mass spectrometry step is performed using a peptide solution obtained by treating the protein solution prepared in this way or a treated product thereof with a proteolytic enzyme as a sample (FIG. 5).

According to such an embodiment, there is no need to separately prepare a sample in the immunoassay step and a sample in the mass spectrometry step. In addition, a solution obtained by the same treatment is analyzed in the immunoassay step and the mass spectrometry step. Therefore, correlation between detection results obtained in these two steps is improved, and a detection result with higher accuracy can be obtained.

As described above, a protein solution obtained by treating a sample with an ionic surfactant may be directly subjected to the mass spectrometry step. Alternatively, the protein solution may be subjected to lyophilization, ultrafiltration, and precipitation/resuspension to remove the ionic surfactant, and then may be subjected to the mass spectrometry step. As a precipitation/resuspension method, any method such as TCA precipitation, acetone precipitation, or TCA/acetone precipitation may be adopted.

As the proteolytic enzyme, an enzyme used for analyzing a protein with a mass spectrometer can be normally used without limitation. Specific examples of the enzyme include trypsin, chymotrypsin, Asp-N, Glu-C, and Lys-C.

In a preferable embodiment of the present invention, the immunoassay step may be performed as a step of determining whether to perform the mass spectrometry step. According to such an embodiment, it is possible to reduce cost of the mass spectrometry step and to improve economic efficiency. Description will be made with reference to FIGS. 6 to 8.

Figure 6:
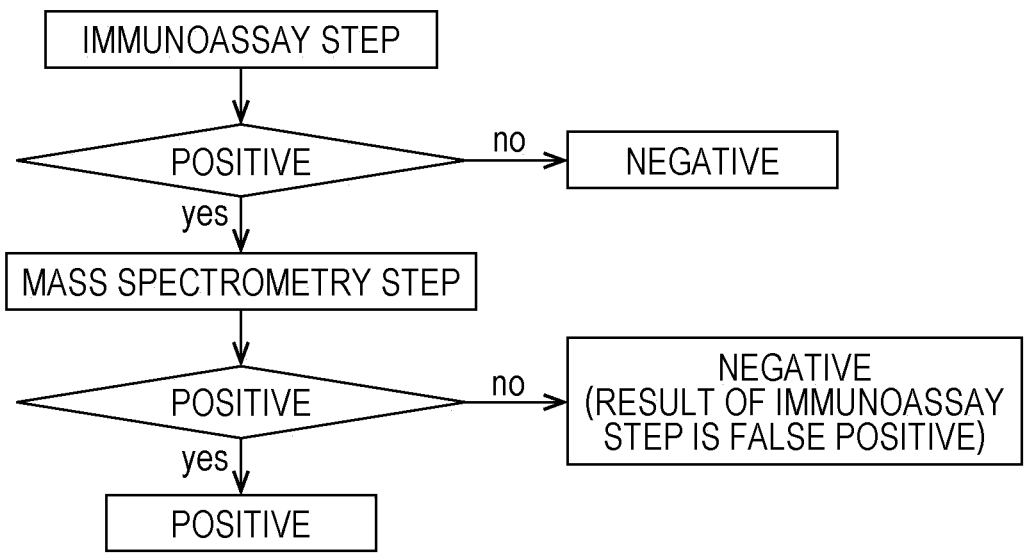
FIG. 6 is a diagram schematically illustrating an embodiment of performing a mass spectrometry step in a case where a result of an immunoassay step is positive.

(i) An embodiment in which the mass spectrometry step is performed in a case where a result of the immunoassay step is positive (FIG. 6)

According to such an embodiment, false positive included in a result of the immunoassay step can be eliminated, and the embodiment is useful in order to accurately quantify the content of a specific protein contained in a positive sample. According to such an embodiment, a negative sample does not need to be subjected to mass spectrometry, and therefore the embodiment has excellent economic efficiency.

Figure 7:
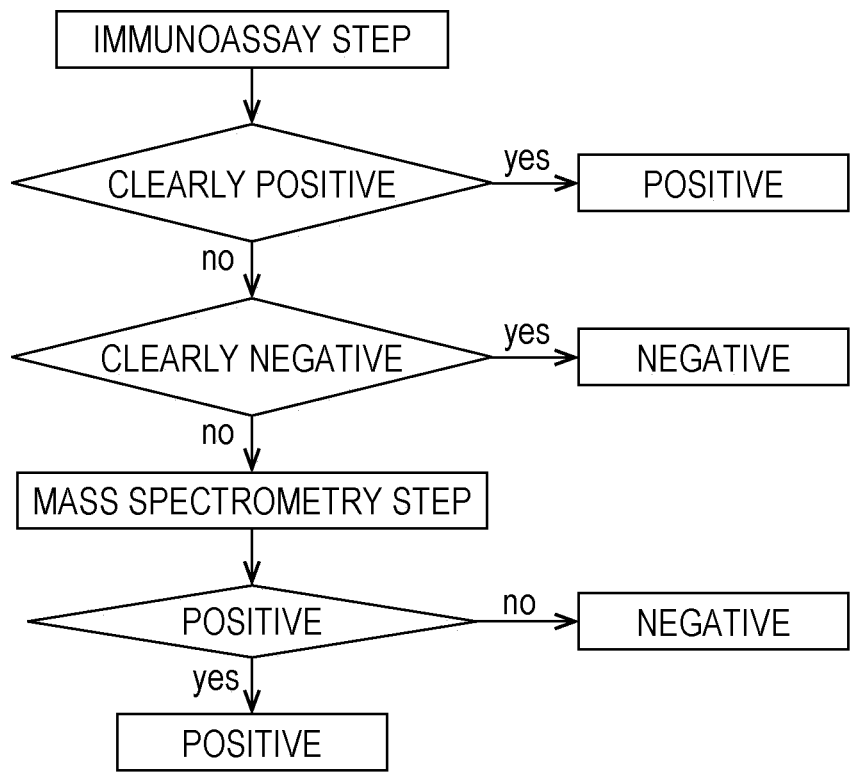
FIG. 7 is a diagram schematically illustrating an embodiment of performing a mass spectrometry step in a case where it is difficult to determine whether a result of an immunoassay step is positive or negative.

(ii) An embodiment in which the mass spectrometry step is performed in a case where it is difficult to determine whether a result of the immunoassay step is positive or negative (FIG. 7)

The embodiment is useful in a case where there is no accurate quantification of a specific protein for a clearly positive sample. A clearly positive sample does not need to be subjected to mass spectrometry, and therefore the embodiment has excellent economic efficiency.

The present embodiment is also preferable in a case where accurate determination between positive and negative is necessary.

Figure 8:
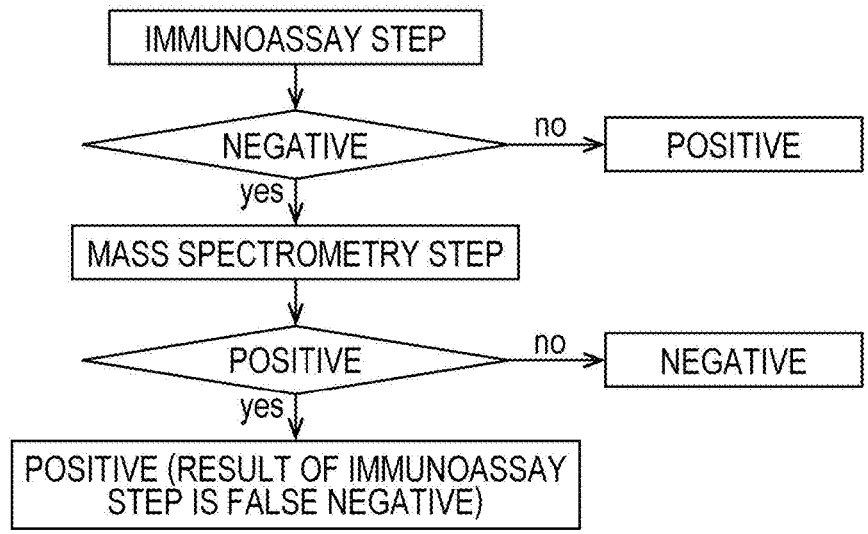
FIG. 8 is a diagram schematically illustrating an embodiment of performing a mass spectrometry step in a case where a result of an immunoassay step is negative.

(iii) An embodiment in which the mass spectrometry step is performed in a case where a result of the immunoassay step is negative (FIG. 8)

According to such an embodiment, false positive included in a result of the immunoassay step can be eliminated. In addition, the embodiment is useful in order to find a sample containing a protein as a detection target although the content of the protein is equal to or less than a detection limit of an antibody used in the immunoassay step.

Figure 9:
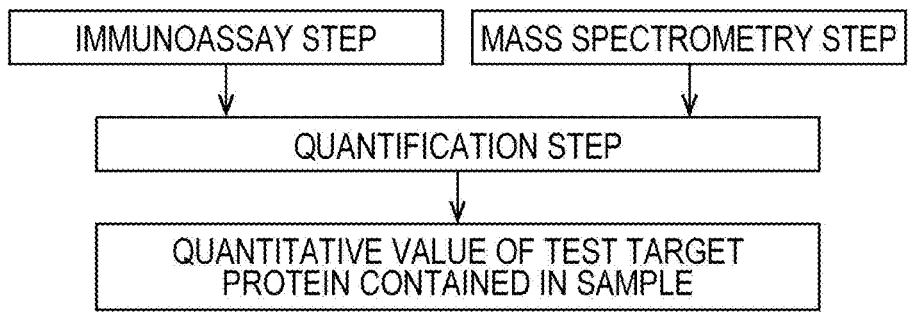
FIG. 9 is a diagram schematically illustrating an embodiment including a quantitative step of comparing a detection result obtained by an immunoassay step with a detection result obtained by a mass spectrometry step and calculating a quantitative value of the content of a specific protein in a sample.

An embodiment of the present invention preferably includes a quantitative step of comparing a detection result obtained in the immunoassay step with a detection result obtained in the mass spectrometry step and calculating a quantitative value of the content of a specific protein in a sample (FIG. 9).

A method for calculating the quantitative value is not particularly limited. Any method for calculating the quantitative value by comparing quantitative values obtained in analysis steps and performing various calculations can be adopted.

In the present invention, in order to improve quantitativeness of a detection result of a specific protein, it is preferable to use a standard solution containing a specific protein the concentration of which is known or a partial peptide thereof in the immunoassay step and the mass spectrometry step.

In a preferable embodiment of the present invention, a solution of a standard peptide which is a partial peptide of a specific protein, to which an anti-peptide antibody can be bonded, and which contains at least a part of an amino acid sequence constituting a mass spectrometry target peptide fragment, is used as a standard solution.

Preferable examples of the standard peptide include a full-length specific protein, an antigen peptide, and a mass spectrometry target peptide fragment.

More preferably, standard solutions containing the same standard peptide are used in the immunoassay step and the mass spectrometry step. According to such an embodiment, standardization between different measurement methods of immunoassay and mass spectrometry is possible.

The immunoassay step and the mass spectrometry step may be performed by different business operators.

For example, as described in the above (i) to (iii), one business operator may perform the immunoassay step as a step of determining whether a sample is subjected to the mass spectrometry step, and another business operator may perform the mass spectrometry step for a sample selected based on the result.

Such an embodiment has excellent economic efficiency, for example, a business operator not having a mass spectrometer does not need to purchase a mass spectrometer.

In a case where the immunoassay step and the mass spectrometry step are performed by different business operators, samples analyzed in the immunoassay step and the mass spectrometry step are preferably peptide solutions obtained by treating the same protein solution prepared by treating a sample with an aqueous solvent containing an ionic surfactant or a treated product thereof with a proteolytic enzyme.

According to such an embodiment, it is possible to prevent occurrence of a measurement error caused by a difference in a method for preparing a sample between business operators.

The kind of the specific protein is not particularly limited. In particular, the present invention is useful for detecting an allergen protein. Examples of the allergen protein include an allergen protein contained in a plant-derived allergen such as pollen or a vegetable food, an animal food, an insect, a mite, a parasite in an animal body, or an animal-derived allergen such as an animal hair or an animal epithelial tissue. More specifically, examples of the pollen allergen include a Gramineae plant belonging to *Triticum, Agrostis*, or *Paspalum*; a Gramineae plant such as Anthoxanthum odoratum, bermuda grass, *Dactylis glomerata*, meadow fescue, rye grass, timothy grass, common reed, Kentucky bluegrass, Sorghum halepense, *Bromus inermis Leyss*, rye, *Holcus lanatus, Avena sativa*, or foxtail; weeds other than Gramineae, such as Taraxacum, *Salsola*, Xanthium, Atriplex, Parietaria, or Urticaceae; weeds other than Gramineae, such as ragweed, *Ambrosia psilostachya* DC., *Ambrosia trifida, Parthenium hysterophorus, Artemisia absinthium, Artemisia princeps pampan, Leucanthemum vulgare*, plantago lanceolata, lamb's-quarter, *Solidago japonica, Amaranthus retroflexus, Kochia littorea, Rumex acetosella*, or humulus japonicus; trees belonging to Acer, *Alnus, Betula, Hazel, Fagus, Juniperus, Quercus, Ulmus, Walnut, Salix, Populus, Fraxinus, Pinus, Eucalyptus, Acacia*, or *Morus*; and trees such as *Platanus acerifolia* Willd., cedar, cypress, pecan, or olive. Examples of the food allergen include cereals including gluten, crustaceans, egg, fish, peanut, soybean, milk, and nuts, specified by the International Food Standards (CODEX) Committee; egg, milk, wheat, buck wheat, peanut, shrimp, crab, abalone, squid, salmon roes, orange, kiwi fruit, beef, walnut, salmon, mackerel, soybean, chicken, pork, matsutake mushroom, peach, yam, apple, gelatin, banana, sesame, and cashew nuts, specified by the Japanese Ministry of Health, Labor, and Welfare; and milk, egg, fish, crustaceans, nuts, wheat, peanut, and soybean, specified by the United States. More specifically, examples of the allergen which is a vegetable food include cereals such as wheat, rye, barley, oat, corn, rice, buckwheat, millet, Foxtail millet, and barnyard millet; beans or nuts such as almond, coconut, peanut, soybean, pea, green bean, hazel, and Brazil nuts; fruits and vegetables such as strawberry, orange, kiwi, potato, celery, onion, tomato, parsley, carrot, garlic, mango, melon, apple, pumpkin, grapefruit, cherry, pear, sweet potato, bamboo shoots, and spinach; sesame; and mustard. Examples of another plant-derived allergen include rubber latex. Examples of the allergen which is an animal food include meat such as pork, chicken, and lamb; fish and shellfish such as cod, crab, shrimp, tuna, salmon, mussel, lobster, mackerel, horse mackerel, sardine, squid, and octopus; egg white, yolk, milk, and cheese. Examples of the allergen which is an insect include insects belonging to *Aedes aegypti* and *Chironomus dilutus*, bee, wasp, polistes wasp, cockroach, and moth. Examples of the allergen which is a mite include *Dermatophagoides pteronyssinus, Dermatophagoides farinae, Acarus siro, Glycyphagus destructor, Tyrophagus putrescentiae*, and *Glycyphagus domesticus*. Examples of the allergen which is parasites in an animal body include *Anisakis*, roundworm, hydatid, and Schistosomatidae. Examples of the allergen which is an animal hair or an animal epithelial tissue include a cat epithelial tissue, a dog epithelial tissue, horse skin chips, bovine skin chips, dog skin chips, a guinea pig epithelial tissue, a goat epithelial tissue, a sheep epithelial tissue, a rabbit epithelial tissue, a pig epithelium tissue, a hamster epithelial tissue, a rat epithelial tissue, a mouse epithelial tissue, goose feathers, chicken feathers, duck feathers, and budgerigar feathers. Examples of another animal-derived allergen include serum of a budgerigar, droppings of a budgerigar, droppings of a pigeon, and urine of a mouse.

A sample in the present invention is not particularly limited, and examples thereof include foods, cosmetics, pharmaceuticals, clothing articles, and a biological sample. The method of the present invention is particularly preferably applied to detection of a specific protein in a food sample.

<2> Method for Designing Antigen Peptide for Producing Anti-Peptide Antibody

The present invention also relates to a method for designing an antigen peptide for producing an anti-peptide antibody used for the above-described method for detecting a specific protein.

In the present invention, first, mass spectrometry is performed using a peptide solution obtained by treating a specific protein with a proteolytic enzyme as a sample to obtain a chromatograph or a mass spectrum.

Subsequently, a peptide fragment corresponding to a signal detected with an intensity preferably of 50% or more, more preferably of 70% or more, still more preferably of 90% or more, further still more preferably of 100%, of a signal detected with the highest intensity, is selected.

Then, a partial peptide of a specific protein containing the same amino acid sequence as an amino acid sequence constituting the selected peptide fragment in four or more amino acid residues, preferably six or more amino acid residues, more preferably ten or more amino acid residues is used as an antigen candidate.

According to the designing method of the present invention, a peptide fragment having an amino acid sequence overlapping with a peptide fragment that can be detected with good sensitivity in the mass spectrometry step can be designed as an antigen peptide. That is, an anti-peptide antibody produced by an antigen peptide designed by this designing method can improve correlation between a result of the immunoassay step and a result of the mass spectrometry step in the above-described detection method of the present invention.

The method for designing an antigen peptide of the present invention may further include a step of selecting a partial peptide containing an amino acid sequence having low homology among species in a specific protein as an antigen candidate.

Specifically, a partial peptide of a specific protein having an amino acid sequence in which homology with an orthologous protein as a specific protein in another species is preferably 70% or less, more preferably 50% or less, and still more preferably 30% or less is selected as an antigen candidate.

By adding such a step, it is possible to select an anti-peptide antibody that hardly causes a cross reaction.

Here, "another species" includes not only a species of immune animal but also an arbitrarily set species.

In the above-described method for detecting a specific protein, in a case where a protein solution obtained by treating a sample with an ionic surfactant is subjected to the immunoassay step, in a steric structure of a specific protein, either a peptide having an amino acid sequence exposed to a molecular surface or a peptide having an amino acid sequence buried in a molecule can be used as an antigen candidate. This is because a specific protein is denatured by the treatment with an ionic surfactant and an amino acid sequence buried in a molecule is exposed.

In the designing method of the present invention, the peptide length of an antigen peptide to be designed is preferably 5 to 50 amino acid residues, more preferably 8 to 20 amino acid residues, and still mote preferably 10 to 15 amino acid residues.

Description in <1> of paragraph 0066 and the following paragraphs of the present specification can be applied to the method for producing an anti-peptide antibody using an antigen peptide designed according to the designing method of the present invention.

<3> Method for Screening Sample Subjected to Mass Spectrometry

The present invention also relates to a method for screening a sample subjected to mass spectrometry for detecting a specific protein, characterized by including an immunoassay step of detecting the specific protein contained in a sample by immunoassay using an anti-peptide antibody specifically recognizing a specific amino acid sequence contained in the specific protein.

Description in (i) to (iii) of paragraphs 0106 to 0108 of the present specification and description in <1> of paragraph 0066 and the following paragraphs of the present specification can be applied to the embodiments of the present invention.

<4> Immunoassay

The immunoassay of the present invention includes the following three steps.

(1) A separation step of separating a protein in a sample
(2) A mass spectrometry step of identifying a protein separated in the separation step by mass spectrometry
(3) An immunoassay step of measuring a protein separated in the separation step and contained in the sample by immunoassay using an anti-peptide antibody specifically bonded to the separated protein Hereinafter, each step will be described in detail.

(1) Separation Step

The separation step separates a protein contained in a proteome in a sample. The sample is not particularly limited as long as being a biological system, and examples thereof include a cell, an embryo, a tissue, and an individual. Examples of the cell include a cultured cell and a cell of a unicellular organism. The embryo includes various cells and cell populations at an early stage of development of a multicellular organism. The tissue may be a tissue section. The individual includes an individual of a unicellular organism and an individual of a multicellular organism.

A protein separation method is not particularly limited, but examples thereof include liquid chromatography, electrophoresis, and ultrafiltration. Electrophoresis is particularly preferable.

A method for preparing a sample subjected to each separation method can be performed according to a conventional method.

For the electrophoresis, either normal one-dimensional electrophoresis or two-dimensional electrophoresis may be used, but two-dimensional electrophoresis with high resolution is preferably adopted.

Selection of the kinds of buffer and gel used for electrophoresis and a specific protein spot subjected to a mass spectrometry step, and excision of a specific protein spot from a gel can be performed according to a conventional method.

(2) Mass Spectrometry Step

In the immunoassay of the present invention, the mass spectrometry step identifies a protein separated in the separation step by mass spectrometry.

In the mass spectrometry step, first, a protein separated in the separation step is treated with a proteolytic enzyme to obtain a peptide fragment.

Description of "<1> (3) Mass spectrometry step" above can be applied as it is to an embodiment in the mass spectrometry step of the immunoassay of the present invention, specifically, a proteolytic enzyme, a mass spectrometer, an ion source, and an analysis unit.

Identification of a protein based on a result of mass spectrometry can be performed according to a conventional method. Specifically, a protein sequence database is searched using mass spectral data obtained by measuring a mass spectrum of a fragment peptide mixture, an amino acid sequence best matching the mass spectrum data is found among proteins registered in the database, and a protein can be identified.

(3) Immunoassay Step

In the immunoassay step, a protein separated in the separation step and contained in the sample is measured by immunoassay using an anti-peptide antibody specifically bonded to the separated protein.

The kind of the immunoassay is not particularly limited, and examples thereof include immunoassay using an anti-peptide antibody labeled with a labeling substance, such as immunochromatography or ELISA.

Specifically, the immunoassay step is as described in "<1> (2) Immunoassay step" above.

Preferable examples of the immunoassay include a method for performing an antigen-antibody reaction in the presence of an ionic surfactant. Description of "<1> (2) immunoassay step" above can be applied to an embodiment of the immunoassay.

The immunoassay step preferably includes an extraction step for extracting a specific protein from a sample. An extraction solvent used in the extraction step is not particularly limited but is preferably an aqueous solvent containing an ionic surfactant.

The description of "<1> (2) Immunoassay step" above can be applied to an embodiment of the extraction step.

The immunoassay step can be performed by a sandwich method or a competitive method. Specifically, the immunoassay step is as described in "<1> (2) Immunoassay step" above.

Description of "<1> (2) Immunoassay step" above can be applied to an antibody used in the immunoassay of the present invention and a production method thereof.

In a case where mass spectrometry is performed using a peptide solution obtained by treating an antigen protein with a proteolytic enzyme as a sample, it is preferable to use an anti-peptide antibody produced using a peptide fragment having the same amino acid sequence as a part of an amino acid sequence of a peptide fragment (mass spectrometry target peptide fragment) corresponding to a detectable signal as an antigen peptide (see FIG. 1).

By using such an anti-peptide antibody, correlation between a measurement result in the immunoassay step and a measurement result in the mass spectrometry step can be improved. [0136]

Description of "<1> (1) Detection target" above can be applied to the length of an amino acid sequence portion common to an antigen peptide and a mass spectrometry target peptide fragment, that is, the preferable length of the amino acid sequence (common amino acid sequence) indicated by X in FIG. 1.

An amino acid sequence specifically recognized by an anti-peptide antibody, that is, an epitope sequence may deviate from a common amino acid sequence (FIG. 2). However, a part (FIG. 3) or the whole (FIG. 4) of an amino acid sequence constituting a mass spectrometry target peptide fragment preferably overlaps with the epitope sequence of the anti-peptide antibody.

In a case where mass spectrometry is performed using a peptide solution obtained by treating an antigen protein with a proteolytic enzyme as a sample, the anti-peptide antibody is particularly preferably produced with an antigen having a common amino acid sequence to a peptide fragment corresponding to a signal detected with an intensity preferably of 50% or more, more preferably of 70% or more, still more preferably of 90% or more, further still more preferably of 100%, of a signal detected with the highest intensity.

In the immunoassay step of the immunoassay of the present invention, it is preferable to use an anti-peptide antibody designed based on a result of the mass spectrometry step. That is, it is preferable to adopt an embodiment including the following three steps after the mass spectrometry step.

(A) A selection step of selecting an amino acid sequence containing four or more amino acid residues with high specificity among amino acid sequences constituting a protein separated in the separation step (B) A peptide synthesis step of synthesizing a partial peptide containing an amino acid sequence selected in the selection step (C) An antibody production step of producing the anti-peptide antibody using the partial peptide as an antigen Hereinafter, each step will be described in detail.

(A) Selection Step

The selection step selects an amino acid sequence of an antigen peptide. Specifically, the selection step selects an amino acid sequence containing four or more amino acid residues with high specificity among amino acid sequences constituting a protein separated in the separation step The amino acid sequence with high specificity to be selected only needs to have four or more amino acid residues, but has preferably six or more amino acid residues, and more preferably ten or more amino acid residues.

Here, the "amino acid sequence with high specificity" includes not only an amino acid sequence with high specificity among different species but also an amino acid sequence capable of distinguishing isoforms of the same species and splicing variants derived from the same gene of the same species.

An amino acid sequence with high specificity can be selected using a normally used homology analysis software.

In addition, in the selection step, an amino acid sequence of an antigen peptide may be selected based on a result of the mass spectrometry step. That is, it is preferable to select an amino acid sequence containing a common amino acid sequence to a mass spectrometry target peptide fragment in the mass spectrometry step.

In the selection step, it is preferable to select an amino acid sequence in which the length of a common amino acid is preferably four or more amino acid residues, more preferably six or more amino acid residues, and still more preferably ten or more amino acid residues.

In the selection step, it is preferable to select an amino acid sequence in which the length of the common amino acid sequence is preferably 10% or more, more preferably 20% or more, and still more preferably 30% or more, of the length of an antigen peptide.

Furthermore, in the selection step, it is preferable to select an amino acid sequence containing a common amino acid sequence to a peptide fragment corresponding to a signal detected with an intensity preferably of 50% or more, more preferably of 70% or more, still more preferably of 90% or more, further still more preferably of 100%, of a signal detected with the highest intensity in the mass spectrometry step.

(B) Peptide Synthesis Step

The peptide synthesis step is a step of synthesizing a partial peptide containing an amino acid sequence selected in the selection step, that is, an antigen peptide. A synthesis method is not particularly limited. Examples thereof include a chemical synthesis method and a biological synthesis method for transforming a host microorganism such as *Escherichia coli* or a cultured cell and culturing the transformed host microorganism such as *Escherichia coli*/cultured cell to produce an antigen peptide, as described above.

(C) Antibody Production Step

This step produces an anti-peptide antibody using a partial peptide synthesized by the above method as an antigen. Specifically, the methods (i) and (ii) of "<1> (2) Immunoassay step" above can be applied as they are.

A measurement result highly correlated with the mass spectrometry step can be obtained by using, in the immunoassay step, an anti-peptide antibody produced in the above steps (A) to (C).

<5> Method for Designing Antigen Peptide

The present invention also relates to a method for designing an antigen peptide for an anti-peptide antibody capable of realizing immunoassay highly correlated with mass spectrometry among amino acid sequences constituting an antigen peptide.

The present invention is characterized in that a partial peptide in which at least four amino acid residues are the same as those of a mass spectrometry target peptide fragment used for performing mass spectrometry using a peptide solution obtained by treating an antigen protein with a proteolytic enzyme as a sample is used as a first antigen candidate.

Description in the above item "<4> (A) Selection step" can be applied to selecting the first antigen candidate.

In a preferable embodiment of the designing method of the present invention, a partial peptide containing an amino acid sequence with high specificity among the first antigen candidates is used as a second antigen candidate.

Description in the above item "<4> (A) Selection step" can also be applied as it is to a specific embodiment in selecting the second antigen candidate.

The designing method of the present invention is preferably applied to designing an antigen peptide of an anti-peptide antibody used in immunoassays that performs an antigen-antibody reaction in the presence of an ionic surfactant.

Description of "<4> (3) Immunoassay step" above can be applied as it is to immunoassay that performs an antigen-antibody reaction in the presence of an ionic surfactant.

The designing method of the present invention is preferably applied to a method for designing an anti-peptide antibody used in the immunoassay of the present invention described in the above item <4>.

<6> Method for Producing Anti-Peptide Antibody

A method for producing an anti-peptide antibody is used for detecting an antigen protein by immunoassay.

The production method of the present invention is characterized in that a partial peptide having a common amino acid sequence (at least four amino acid residues) to a mass spectrometry target peptide fragment used for performing mass spectrometry using a peptide solution obtained by treating an antigen protein with a proteolytic enzyme as a sample is used as an antigen peptide.

Description on the antigen peptide in the above item "<4> (3) Immunoassay step" can be applied to the antigen peptide.

The antigen peptide preferably contains an amino acid sequence with high specificity among amino acid sequences constituting an antigen protein. Description in the above item "<4> (A) Selection step" can be applied to the "amino acid with high specificity".

In the production method of the present invention, an anti-peptide antibody is produced using the above-described antigen peptide for an immune animal. The methods (i) and (ii) described in the above item "<1> (2) Immunoassay step" can be applied to a specific immunization method in the production method of the present invention.

It is preferable to apply the production method of the present invention to producing an anti-peptide antibody used in immunoassay that performs an antigen-antibody reaction in the presence of an ionic surfactant.

Description of "<4> (3) Immunoassay step" above can be applied as it is to immunoassay that performs an antigen-antibody reaction in the presence of an ionic surfactant.

<7> Anti-Peptide Antibody

The present invention relates to an anti-peptide antibody produced by an antigen peptide designed by the above designing method, and an anti-peptide antibody produced by the above-described production method.

The anti-peptide antibody in the present invention can realize immunoassay capable of obtaining a result highly correlated with mass spectrometry.

Therefore, the anti-peptide antibody in the present invention is preferably applied to detection of a protein identified by mass spectrometry. Furthermore, if the anti-peptide antibody in the present invention is applied to detection of a protein identified in proteomics, qualitative or quantitative measurement of a specific protein in proteome, which has been a recent problem in the field of proteomics, can be realized.

The anti-peptide antibody in the present invention can be easily evaluated for its specificity or correlation with a result of mass spectrometry by an evaluation method including an immunoassay step, a mass spectrometry step, and an evaluation step.

The form of a sample subjected to the immunoassay step and the mass spectrometry step is not particularly limited as long as it is guaranteed that the sample contains an antigen protein.

As the sample subjected to the immunoassay step and the mass spectrometry step, a standard solution in which the concentration of an antigen protein is known is preferably used. In addition, preferably, the sample does not contain a protein other than an antigen protein or a peptide.

Description in the above item "<4> can be applied to specific embodiments of the immunoassay step and the mass spectrometry step.

The evaluation step compares results of the immunoassay step and the mass spectrometry step with each other. Samples that have been subjected to the two steps each contain an antigen protein, and therefore both steps should exhibit positive results. In a case where both steps exhibit positive results as described above, the anti-peptide antibody used detects the same protein as a protein to be detected by mass spectrometry. In this case, the anti-peptide antibody can be evaluated as being able to be subjected to immunoassay correlated with mass spectrometry.

Meanwhile, in a case where a result of either one of the steps is positive and a result of the other step is negative, the anti-peptide antibody detects a different protein from a protein to be detected by mass spectrometry. In this case, the anti-peptide antibody can be evaluated as not being able to be subjected to immunoassay correlated with mass spectrometry.

As a reason why the results of the two steps do not coincide with each other, it is considered that there is an error in identification of a protein in mass spectrometry or there is a problem in specificity of the anti-peptide antibody.

EXAMPLES

Hereinafter, Examples of the protein detection method and the immunoassay of the present invention will be described.

<1> Separation Step

Samples A and B each containing a plurality of proteins and simulating a proteome were prepared.

Figure 10:
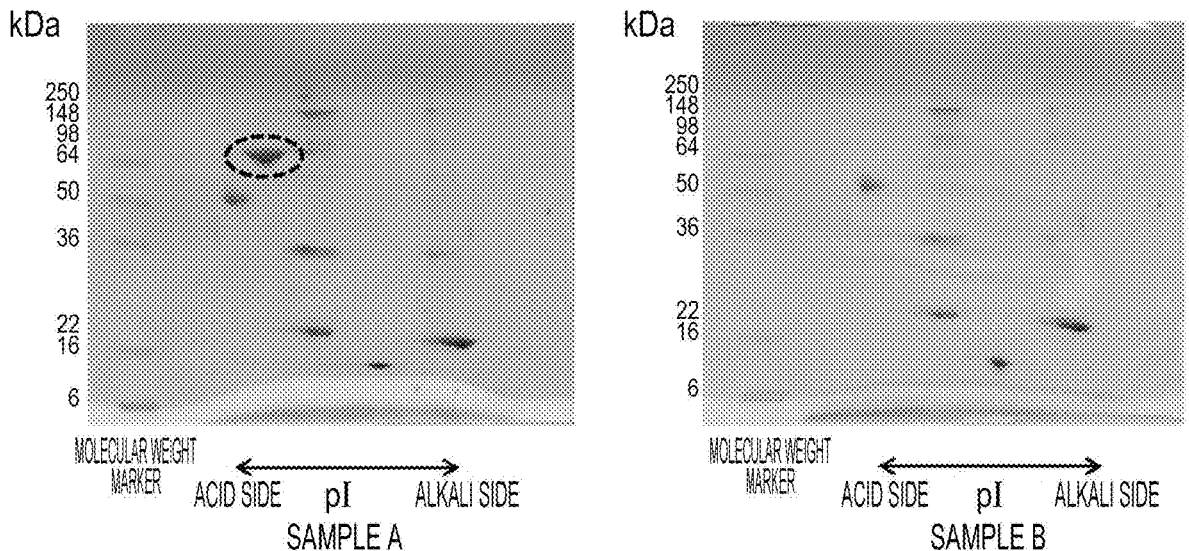
FIG. 10 is a staining diagram obtained by staining a gel after two-dimensional electrophoresis of samples A and B with Coomassie blue. The spot surrounded by the dotted line is a protein spot characteristically detected in sample A.

Samples A and B were each electrophoresed on an immobilized pH gradient isoelectric focusing gel, and a protein contained in each of the samples was separated. FIG. 10 illustrates a staining diagram in which the gel after electrophoresis was stained with Coomassie blue.

<2> Mass Spectrometry Step

Figure 11:
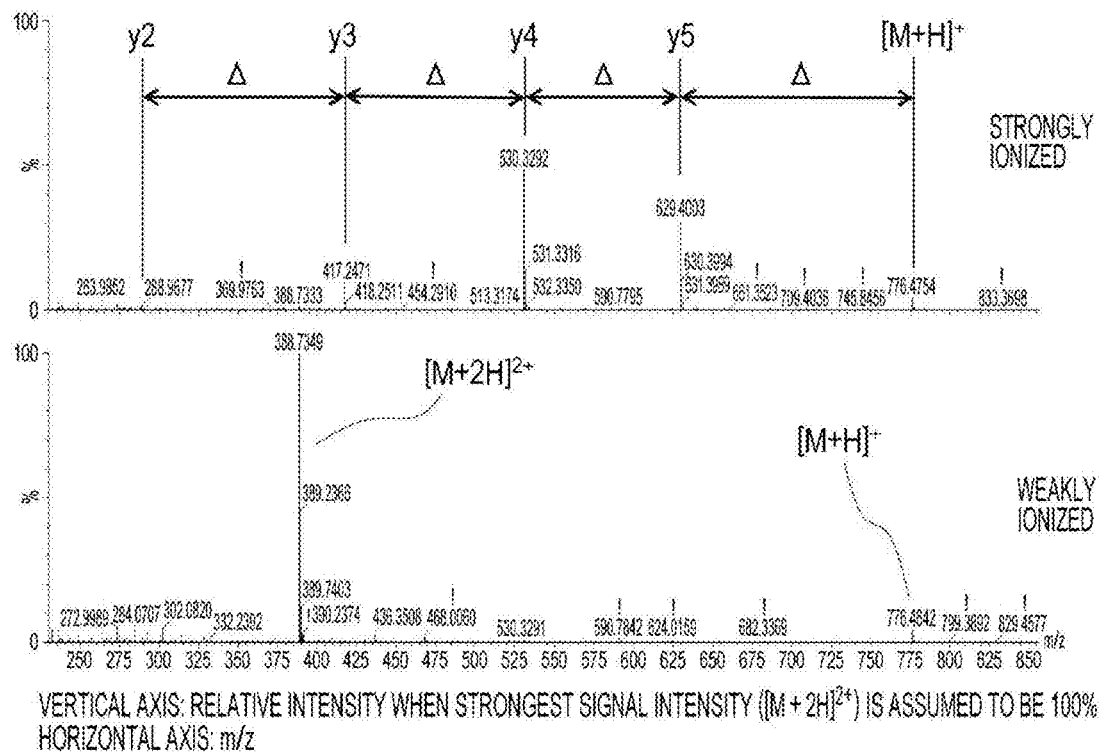
FIG. 11 is a mass spectrum of a specific peptide fragment contained in a protein digest of the spot characteristic to the electrophoretic map of sample A. The upper row illustrates a spectrum obtained by strongly setting a voltage in an ionization step to generate a fragment ion. The lower row illustrates a spectrum obtained by weakly setting a voltage in an ionization step to generate two kinds of protonated ions ($[M+H]^+$ and $[M+2H]^{2+}$) of the same peptide fragment.

A spot characteristic to the electrophoresis diagram of sample A and surrounded by the dotted line in FIG. 10 was cut out, and reduction, alkylation, and digestion (trypsin) were performed in the gel. Using this digest as a sample, mass spectrometry was performed by LC-TOFMS to obtain a mass spectrum. FIG. 11 illustrates an example thereof. The upper row of FIG. 11 illustrates a spectrum obtained by strongly setting a voltage in an ionization step to generate a fragment ion. The lower row of FIG. 11 illustrates a spectrum obtained by weakly setting a voltage in an ionization step to generate two kinds of protonated ions ($[M+H]^+$ and $[M+2H]^{2+}$) of the same peptide fragment.

As a result of comparing data of a plurality of peptide fragments detected by mass spectrometry in this way with a database, it was identified that a protein separated by two-dimensional electrophoresis was a porcine serum albumin. In addition, it was found that a peptide fragment corresponding to the mass spectrum of FIG. 11 had a FVIEIR sequence (SEQ ID NO: 59) in amino acid one letter notation.

<3> Production of Anti-Peptide Antibody (1) Selection of Antigen Peptide

Table 1 illustrates the whole sequence of a porcine serum albumin. In a case where this porcine serum albumin is cleaved with trypsin, if it is assumed that cleavage occurs also in a case where lysine and arginine in the sequence are consecutive, cleavage theoretically occurs at 87 sites, resulting in generation of 88 fragments in total (Table 2).

TABLE 1

| Sequence of porcine serum albumin (607 amino acid) |
|---|
| SEQ ID NO 1 |
| MKWVTFISLLFLFSSAYSRGVFRRDTYKSEIAHRFKDLGEQYFKGLVLIA |
| FSQHLQQCPYEEHVKLVREVTEFAKTCVADESAENCDKSIHTLFGDKLC |
| AIPSLREHYGDLADCCEKEEPERNECFLQHKNDNPDIPKLKPDPVALCA |
| DFQEDEQKFWGKYLYEIARRHPYFYAPELLYYAIIYKDVFSECCQAADK |
| AACLLPKIEHLREKVLTSAAKQRLKCASIQKFGERAFKAWSLARLSQRF |
| PKADFTEISKIVTDLAKVHKECCHGDLLECADDRADLAKYICENQDTIS |
| TKLKECCDKPLLEKSHCIAEAKRDELPADLNPLEHDFVEDKEVCKNYKE |
| AKHVFLGTFLYEYSRRHPDYSVSLLLRIAKIYEATLEDCCAKEDPPACYA |
| TVFDKFQPLVDEPKNLIKQNCELFEKLGEYGFQNALIVRYTKKVPQVSTP |
| TLVEVARKLGLVGSRCCKRPEEERLSCAEDYLSLVLNRLCVLHEKTPVS |
| EVTKCCTESLVNRRPCFSALTDETYKPKEFVEGTFTFHADLCTLPEDE |
| KQIKKQTALVELLKHKPHATEEQLRTVLGNFAAFVQKCCAAPDHEACFA |
| VEGPKFVIEIRGILA |

TABLE 2

| peptide No. | Sequence | Number of amino acids | SEQ ID NO |
|---|---|---|---|
| 1 | MK | 2 | — |
| 2 | WVTFISLLFLFSSAYSR | 17 | 2 |
| 3 | GVFR | 4 | 3 |

TABLE 2-continued

| peptide No. | Sequence | Number of amino acids | SEQ ID NO |
|---|---|---|---|
| 4 | R | 1 | — |
| 5 | DTYK | 4 | 4 |
| 6 | SEIAHR | 6 | 5 |
| 7 | FK | 2 | — |
| 8 | DLGEQYFK | 8 | 6 |
| 9 | GLVLIAFSQHLQQCPYEEHVK | 21 | 7 |
| 10 | LVR | 3 | — |
| 11 | EVTEFAK | 7 | 8 |
| 12 | TCVADESAENCDK | 13 | 9 |
| 13 | SIHTLFGDK | 9 | 10 |
| 14 | LCAIPSLR | 8 | 11 |
| 15 | EHYGDLADCCEK | 12 | 12 |
| 16 | EEPER | 5 | 13 |
| 17 | NECFLQHK | 8 | 14 |
| 18 | NDNPDIPK | 8 | 15 |
| 19 | LK | 2 | — |
| 20 | PDPVALCADFQEDEQK | 16 | 16 |
| 21 | FWGK | 4 | 17 |
| 22 | YLYEAIAR | 7 | 18 |
| 23 | R | 1 | — |
| 24 | HPYFYAPELLYYAIIYK | 17 | 19 |
| 25 | DVFSECCQAADK | 12 | 20 |
| 26 | AACLLPK | 7 | 21 |
| 27 | IEHLR | 5 | 22 |
| 28 | EK | 2 | — |
| 29 | VLTSAAK | 7 | 23 |
| 30 | QR | 2 | — |
| 31 | LK | 2 | — |
| 32 | CASIQK | 6 | 24 |
| 33 | FGER | 4 | 25 |
| 34 | AFK | 3 | — |
| 35 | AWSLAR | 5 | 26 |
| 36 | LSQR | 4 | 27 |
| 37 | FPK | 3 | — |
| 38 | ADFTEISK | 8 | 28 |
| 39 | IVTDLAK | 7 | 29 |
| 40 | VHK | 3 | — |
| 41 | ECCHGDLLECADDR | 14 | 30 |

TABLE 2-continued

| peptide No. | Sequence | Number of amino acids | SEQ ID NO |
|---|---|---|---|
| 42 | ADLAK | 5 | 31 |
| 43 | YICENQDTISTK | 12 | 32 |
| 44 | LK | 2 | — |
| 45 | ECCDK | 5 | 33 |
| 46 | PLLEK | 5 | 34 |
| 47 | SHCIAEAK | 8 | 35 |
| 48 | R | 1 | — |
| 49 | DELPADLNPLEHDFVEDK | 18 | 36 |
| 50 | EVCK | 4 | 37 |
| 51 | NYK | 3 | — |
| 52 | EAK | 3 | — |
| 53 | HVFLGTFLYEYSR | 13 | 38 |
| 54 | R | 1 | — |
| 55 | HPDYSVSLLLR | 11 | 39 |
| 56 | IAK | 3 | — |
| 57 | IYEATLEDCCAK | 12 | 40 |
| 58 | EDPPACYATVFDK | 13 | 41 |
| 59 | FQPLVDEPK | 9 | 42 |
| 60 | NLIK | 4 | 43 |
| 61 | QNCELFEK | 8 | 44 |
| 62 | LGEYGFQNALIVR | 13 | 45 |
| 63 | YTK | 3 | — |
| 64 | K | 1 | — |
| 65 | VPQVSTPTLVEVAR | 14 | 46 |
| 66 | K | 1 | — |
| 67 | LGLVGSR | 7 | 47 |
| 68 | CCK | 3 | — |
| 69 | R | 1 | — |
| 70 | PEEER | 5 | 48 |
| 71 | LSCAEDYLSLVLNR | 14 | 49 |
| 72 | LCVLHEK | 7 | 50 |
| 73 | TPVSEK | 6 | 51 |
| 74 | VTK | 3 | — |
| 75 | CCTESLVNR | 9 | 52 |
| 76 | R | 1 | — |
| 77 | PCFSALTPDETYK | 13 | 53 |
| 78 | PK | 2 | — |
| 79 | EFVEGTFTFHADLCTLPEDEK | 21 | 54 |
| 80 | QIK | 3 | — |
| 81 | K | 1 | — |
| 82 | QTALVELLK | 9 | 55 |
| 83 | HK | 2 | — |
| 84 | PHATEEQLR | 9 | 56 |
| 85 | TVLGNFAAFVQK | 12 | 57 |
| 86 | CCAAPDHEACFAVEGPK | 17 | 58 |
| 87 | FVIEIR | 6 | 59 |
| 88 | GILA | 4 | 60 |

Among the peptide fragments illustrated in Table 2, a peptide having four or more amino acids was selected in consideration of specificity (59 in total). The 59 peptide fragments were compared with chromatogram data (FIG. 12) of a trypsin digest of a porcine serum albumin obtained in the mass spectrometry step, and six peptide fragments indicating a strong signal in mass spectrometry and detected with good sensitivity were selected (Table 3).

TABLE 3

| peptide No. | Sequence of amino acid | Specificity | SEQ ID NO |
|---|---|---|---|
| 22 | YLYEIAR | Sequence commonly present in dog, cat, human, and pig | 18 |
| 39 | IVTDLAK | Sequence only present in pig | 29 |
| 43 | YICENQDTISTK | Sequence only present in pig | 32 |
| 82 | QTALVELLK | Sequence commonly present in dog, bovine, sheep, and pig | 55 |
| 87 | FVIEIR | Sequence only present in pig | 59 |
| 88 | GILA | Sequence only present in pig | 60 |

Homology search was performed on the amino sequences of the six peptide fragments illustrated in Table 3 using a database, and the degree of specificity of each of the amino acid sequences was analyzed. Table 3 also illustrates results thereof.

Figure 12:
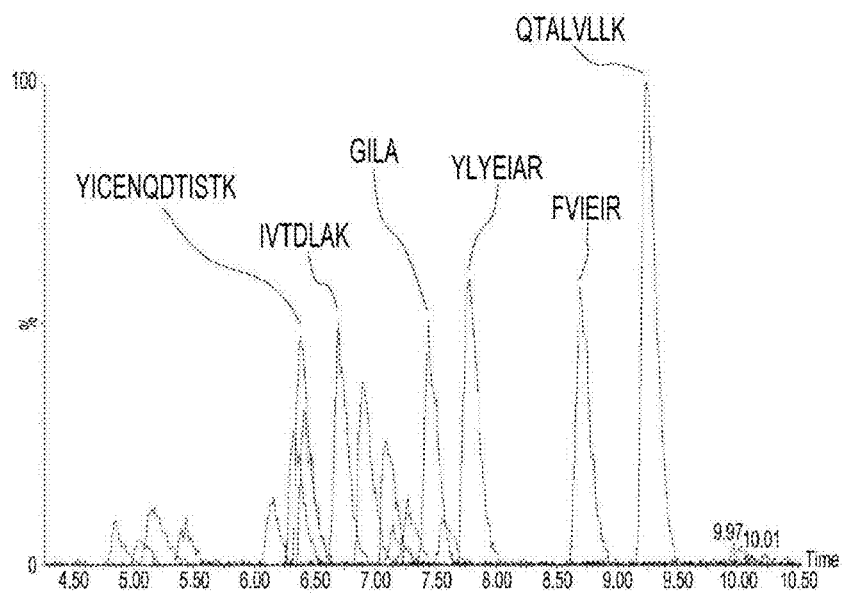
FIG. 12 is a chromatogram obtained by analyzing a trypsin digest of a porcine serum albumin by LC-TOFMS.

Comparison between the chromatogram data of FIG. 12 and the results of Table 3 indicates that a QTALVELLK sequence (SEQ ID NO: 55) and a YLYEIAR sequence (SEQ ID NO: 18) can be detected with good sensitivity in mass spectrometry, but the same sequence also exists in another species of protein, and specificity is poor. Meanwhile, a FVIEIR sequence (SEQ ID NO: 59) and a GILA sequence (SEQ ID NO: 60) were specific to a pig.

Therefore, it was decided to produce an anti-peptide antibody using a peptide formed of PKFVIEIRGILA (SEQ ID NO: 61) containing the FVIEIR sequence (SEQ ID NO: 59) and the GILA sequence (SEQ ID NO: 60) which can be detected with good sensitivity in mass spectrometry and have high specificity as an antigen peptide.

(2) Production of Anti-Peptide Antibody

An anti-peptide antibody recognizing the PKFVIEIRGILA peptide (SEQ ID NO: 61) was prepared by the following procedure.

(2-1) Production of Intermediate Purification Column and Purification Column

An intermediate purification column and a purification column were prepared by the following method.

A purified porcine serum albumin was dissolved at a concentration of 10 mg/mL in a 20 mM sodium phosphate buffer (pH 7.5) containing 150 mM NaCl, 0.6% SDS, and 0.1 M $Na_2SO_3$. The resulting solution was immersed in boiling water for 10 minutes and then cooled with running water.

25 mg of the denatured porcine serum albumin thus obtained was bonded to a 5 mL resin for chromatography at a concentration of 5 mg/mL resin to manufacture an intermediate purification column.

In addition, a peptide in which a cysteine residue was bonded to an N-terminal of the PKFVIEIRGILA peptide (SEQ ID NO: 61) was synthesized. This peptide was bonded via a thiol group of the cysteine residue to a resin for chromatography at a concentration of 100 μg/mL resin to manufacture a purification column.

(2-2) Intermediate Purification Step

An antiserum obtained from a rabbit immunized with a porcine serum albumin treated at 135° C. was centrifuged at 40,000×g for 20 minutes to obtain a supernatant.

150 mL of this supernatant was caused to pass through an intermediate purification column at a flow rate of 1 mL/min and then washed with 60 mL of PBS.

Thereafter, a 0.1 M glycine-HCl buffer (pH 2.3) was caused to pass through the intermediate purification column to elute a polyclonal antibody adsorbed on the column.

The eluate was dispensed into a test tube containing 0.2 mL of 1 M tris-HCl buffer (pH 8.6) in 2 mL portions. Absorbance (A280) at 280 nm was measured for each fraction of the eluate, and a fraction with A280 of 0.5 or more was pooled.

The amount of an antibody thus obtained was about 70 mg (calculated by assuming that A280=1.4=1 mg/mL was satisfied).

The above operation was repeated four times to obtain about 280 mg of a polyclonal anti-denatured porcine serum albumin antibody.

(2-3) Purification Step

The polyclonal anti-denatured porcine serum albumin antibody obtained in the intermediate purification step was caused to pass through a purification column carrying a PKFVIEIRGILA peptide (SEQ ID NO: 61) thereon and then washed with 15 mL of PBS.

Thereafter, a 0.1 M glycine-HCl buffer (pH 2.3) was caused to pass through the purification column to elute a polyclonal anti-peptide antibody adsorbed on the column.

Note that the polyclonal antibody not adsorbed by the purification column was recovered as a polyclonal anti-denatured porcine serum albumin antibody.

The eluate was dispensed into a test tube containing 0.05 mL of 1 M tris-HCl buffer (pH 8.6) in 0.5 mL portions. Absorbance was measured for each fraction of the eluate, and a fractions with A280 of 0.5 or more was pooled.

In this way, about 2 mg of a polyclonal anti-peptide antibody specifically bonded to the amino acid sequence at a C-terminal of a porcine serum albumin was obtained.

<4> Creation of Calibration Curve of ELISA (1) Manufacture of Immobilized Plate

The anti-peptide antibody obtained in the purification step was prepared to 1 μg/mL with a 50 mM sodium carbonate buffer (pH 9.6), dispensed into a 96-well microplate in 0.1 mL portions, and allowed to stand at room temperature for two hours.

Thereafter, the antibody solution was discarded from the wells, and the wells were washed with a 20 mM tris-HCl buffer (pH 7.4) containing 150 mM NaCl and 0.02% Tween 20. Thereafter, the buffer containing 1 mg/mL ovalbumin was dispensed into the wells in 200 μL portions and allowed to stand at room temperature for two hours. In this way, an immobilized plate in which the polyclonal anti-peptide antibody had been immobilized, obtained in the purification step, was manufactured. The immobilized plate was stored at 4° C. until use.

(2) ELISA

The polyclonal anti-denatured porcine serum albumin antibody that had not been adsorbed by the purification column was labeled with horseradish peroxidase to prepare a labeled antibody.

A purified porcine serum albumin was dissolved at a concentration of 10 mg/mL in 20 mM tris-HCl (pH 7.4) containing 0.6% SDS, 0.1 M sodium sulfite, 0.05% Tween 20, and 1 mg/mL BSA. The resulting mixture was heated in boiling water for 10 minutes and cooled in running water to obtain a solution containing a denatured porcine serum albumin.

This solution was diluted with 20 mM tris-HCl (pH 7.4) containing 150 mM NaCl, 0.05% Tween 20, and 1 mg/mL BSA to prepare a denatured porcine serum albumin standard solution having the concentration illustrated in Table 1.

Then, ELISA measurement with the labeled antibody and the immobilized plate was performed using the standard solution by a conventional method, and a calibration curve was created. That is, the standard solution was dispensed into the wells of the immobilized plate and allowed to stand. After the standard solution was allowed to stand, the wells were washed with a buffer, a substrate solution was put into the wells, and colorimetric quantification was performed.

Figure 13:
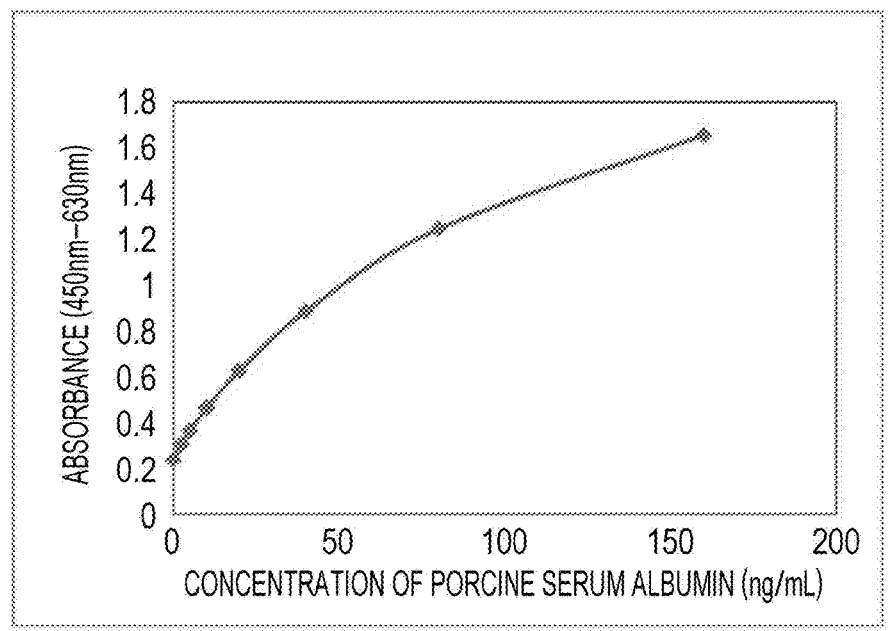
FIG. 13 is a calibration curve of a porcine serum albumin created by ELISA.

Table 4 illustrates the concentration of a denatured porcine serum albumin in the standard solution and a result of colorimetric quantification. FIG. 13 illustrates a calibration curve.

TABLE 4

| | Concentration of porcine serum albumin (ng/mL) | | | | | | | |
| --- | --- | --- | --- | --- | --- | --- | --- | --- |
| | 0 | 2.5 | 5 | 10 | 20 | 40 | 80 | 160 |
| Absorbance (450 nm-630 nm) | 0.24 | 0.306 | 0.368 | 0.467 | 0.628 | 0.887 | 1.245 | 1.657 |

<5> Creation of Calibration Curve of LC-MS/MS

Figure 15:
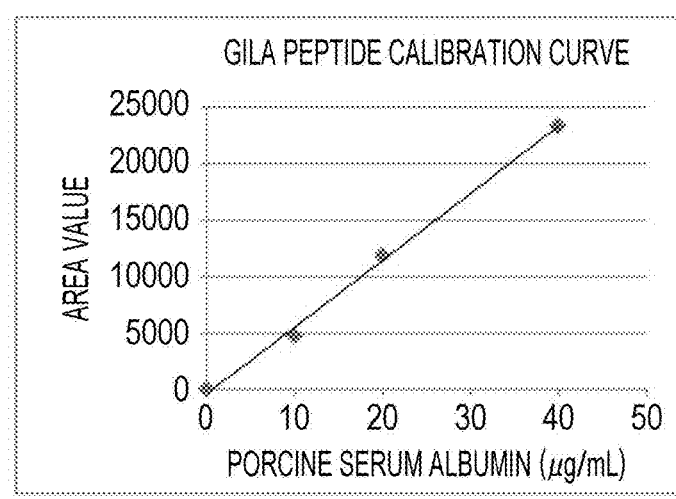
FIG. 15 is a calibration curve of a porcine serum albumin created based on an area value of a GILA peptide ion (SEQ ID NO: 60) obtained as a result of mass spectrometry by LC-MS/MS.
Figure 16:
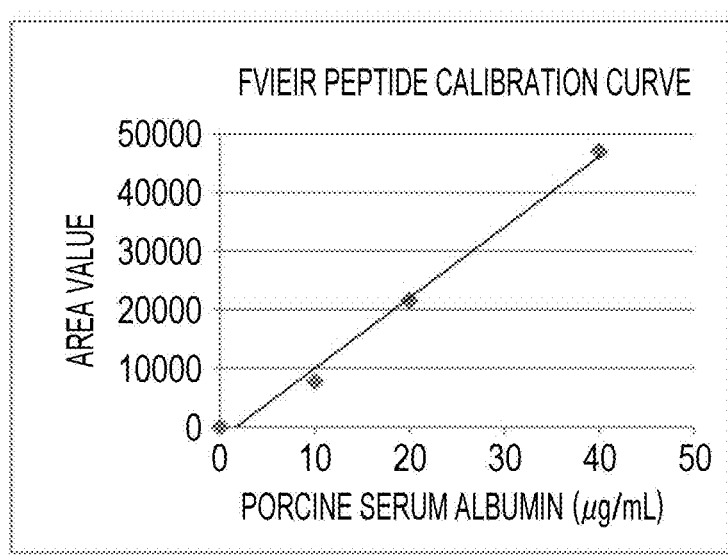
FIG. 16 is a calibration curve of a porcine serum albumin created based on an area value of a FVIEIR peptide ion (SEQ ID NO: 59) obtained as a result of mass spectrometry by LC-MS/MS.

Among the same denatured porcine serum albumin standard solutions as that used for creating the calibration curve of ELISA, those containing 0 μg/mL, 10 μg/mL, 20 μg/mL, and 40 μg/mL denatured porcine serum albumin were enzymatically digested with trypsin. Then, mass spectrometry was performed by tandem type LC-MS/MS including two quadrupole type analysis units using this trypsin enzyme digested solution as a sample. Specifically, ions corresponding to the GILA peptide (SEQ ID NO: 60) and the FVIEIR peptide (lower row in FIG. 14) (SEQ ID NO: 59) generated by enzymatic digestion of the denatured porcine serum albumin standard solution with trypsin were used as MRM transitions, and quantitative analysis based on an area value was performed. Table 5 illustrates results thereof, and FIGS. 15 and 16 illustrate calibration curves.

TABLE 5

| | Concentration of porcine serum albumin (µg/mL) | | | |
|---|---|---|---|---|
| | 0 | 10 | 20 | 40 |
| Area value of GILA peptide | 0 | 4805 | 11881 | 23334 |
| Area value of FVIEIR peptide | 0 | 7749 | 21606 | 47077 |

(Measured concentration: µg/mL)

<6> Immunoassay (ELISA)

A porcine serum albumin-added food obtained by adding a purified porcine serum albumin to each of water and milk to have a concentration of 10 µg/mL, 20 µg/mL, or 40 µg/mL was prepared. Water and milk to which no purified porcine serum albumin had been added were also prepared as negative controls.

ELISA was performed using the immobilized plate manufactured above using these porcine serum albumin-added/non-added foods as samples. ELISA was performed with the sample diluted. By applying a result of colorimetric quantification obtained as a result to the calibration curve of FIG. 13, a quantitative value of a porcine serum albumin in each sample was calculated. Table 6 illustrates results thereof.

TABLE 6

| | Concentration of porcine serum albumin in sample | | | |
|---|---|---|---|---|
| Sample | 0 µg/mL Measured concentration | 10 µg/mL Measured concentration | 20 µg/mL Measured concentration | 40 µg/mL Measured concentration |
| Water | 0 | 7.07 | 13.6 | 33.2 |
| Milk | 0 | 8.12 | 16.9 | 31.8 |

(Measured concentration: µg/mL)

<7> Mass Spectrometry (LC-MS/MS)

Mass spectrometry of a porcine serum albumin was performed by LC-MS/MS in a similar manner to the above <5> using the porcine serum albumin-added/non-added foods prepared in the above <6> as samples. By applying area values of a GILA peptide ion (SEQ ID NO: 60) and a FVIEIR peptide ion (SEQ ID NO: 59) in each sample obtained as a result to the calibration curves of FIG. 15 or 16, a quantitative value of a porcine serum albumin in each sample was calculated. Tables 7 and 8 illustrate results thereof.

TABLE 7

Result of quantification of porcine serum albumin by detection of GIAL peptide ion

| | Concentration of porcine serum albumin in sample | | | | | | | |
|---|---|---|---|---|---|---|---|---|
| | 0 µg/mL | | 10 µg/mL | | 20 µg/mL | | 40 µg/mL | |
| Sample | Area value | Measured concentration | Area value | Measured concentration | Area value | Measured concentration | Area value | Measured concentration |
| Water | 0 | 0 | 4866 | 8.8 | 11843 | 20.6 | 23397 | 40.1 |
| Milk | 0 | 0 | 6865 | 12.2 | 12857 | 22.3 | 23931 | 41.0 |

(Measured concentration: µg/mL)

TABLE 8

Result of quantification of porcine serum albumin by detection of FVIEIR peptide ion

| | Concentration of porcine serum albumin in sample | | | | | | | |
|---|---|---|---|---|---|---|---|---|
| | 0 µg/mL | | 10 µg/mL | | 20 µg/mL | | 40 µg/mL | |
| Sample | Area value | Measured concentration | Area value | Measured concentration | Area value | Measured concentration | Area value | Measured concentration |
| Water | 0 | 0 | 7789 | 8.1 | 21418 | 19.4 | 46829 | 40.5 |
| Milk | 0 | 0 | 12099 | 11.7 | 23133 | 20.8 | 51787 | 44.6 |

(Measured concentration: µg/mL)

<8> Summary

Correlation between the result of ELISA of the above <6> and the result of LC-MS/MS of the above <7> was tested. Specifically, a P value was determined for the results obtained by measuring the same sample by ELISA and LC-MS/MS. For LC-MS/MS, correlation with the result of ELISA was determined for the results of detection of a GILA peptide ion (SEQ ID NO: 60) and a FVIEIR peptide ion (SEQ ID NO: 59). Table 9 illustrates results thereof.

TABLE 9

| | Sample | |
|---|---|---|
| | Water | Milk |
| Result of ELISA vs Result of LC-MS/MS (detection of GIAL peptide ion) | p = 0.007 | p = 0.001 |
| Result of ELISA vs Result of LC-MS/MS (detection of FVIEIR peptide ion) | p = 0.004 | p = 0.003 |

As illustrated in Table 9, there is significant correlation between the result of ELISA of the above <6> and the result of LC-MS/MS of the above <7>.

This result indicates that the measurement result by the immunoassay of the present invention is highly correlated with the measurement result by mass spectrometry using a peptide having a common amino acid sequence as a measurement target and has excellent accuracy.

Immunoassay can be performed at low cost with a simple method. However, quantitative measurement by immunoassay generally lacks accuracy.

Meanwhile, mass spectrometry is evaluated to be more accurate than immunoassay. However, there are also disadvantages as a test technique, such as high initial cost and requirement of high expertise in operation or the like of a device.

As described above, there are disadvantages in each of immunoassay and mass spectrometry. However, according to the present invention, by utilizing advantages of immunoassay and mass spectrometry, a method for detecting a specific protein with higher accuracy and higher economic efficiency can be provided.

INDUSTRIAL APPLICABILITY

The present invention can be applied to a food allergy test technique.

In addition, the present invention can be applied to proteomics.

FIG. 1
FULL-LENGTH PROTEIN
ANTIGEN PEPTIDE
MASS SPECTROMETRY TARGET PEPTIDE FRAGMENT

FIG. 2
FULL-LENGTH PROTEIN
ANTIGEN PEPTIDE
MASS SPECTROMETRY TARGET PEPTIDE FRAGMENT EPITOPE

Figure 3:
FIG. 3 is a diagram schematically illustrating a case where a part of an amino acid sequence constituting a mass spectrometry target peptide fragment overlaps with an epitope sequence of an anti-peptide antibody.
Figure 3:
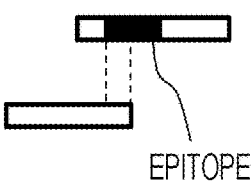

FIG. 3
FULL-LENGTH PROTEIN
ANTIGEN PEPTIDE
MASS SPECTROMETRY TARGET PEPTIDE FRAGMENT EPITOPE

Figure 4:
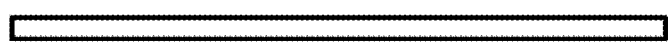
FIG. 4 is a diagram schematically illustrating a case where the whole of an amino acid sequence constituting a mass spectrometry target peptide fragment overlaps with an epitope sequence of an anti-peptide antibody.
Figure 4:
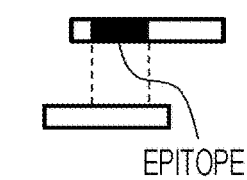

FIG. 4
FULL-LENGTH PROTEIN
ANTIGEN PEPTIDE
MASS SPECTROMETRY TARGET PEPTIDE FRAGMENT EPITOPE

FIG. 5
EXTRACTION STEP (IONIC SURFACTANT)
PROTEIN SOLUTION
MASS SPECTROMETRY STEP
IMMUNOASSAY STEP

FIG. 6
IMMUNOASSAY STEP
POSITIVE, NEGATIVE
MASS SPECTROMETRY STEP POSITIVE, NEGATIVE (RESULT OF IMMUNOASSAY STEP IS FALSE POSITIVE)
POSITIVE

FIG. 7
IMMUNOASSAY STEP
CLEARLY POSITIVE, POSITIVE
CLEARLY NEGATIVE, NEGATIVE
MASS SPECTROMETRY STEP
POSITIVE, NEGATIVE
POSITIVE

FIG. 8
IMMUNOASSAY STEP
NEGATIVE, POSITIVE
MASS SPECTROMETRY STEP
POSITIVE, NEGATIVE
POSITIVE (RESULT OF IMMUNOASSAY STEP IS FALSE NEGATIVE)

FIG. 9
IMMUNOASSAY STEP
MASS SPECTROMETRY STEP
QUANTIFICATION STEP
QUANTITATIVE VALUE OF TEST TARGET PROTEIN CONTAINED IN SAMPLE

FIG. 10
MOLECULAR WEIGHT MARKER
ACID SIDE, ALKALI SIDE
SAMPLE A
MOLECULAR WEIGHT MARKER
ACID SIDE, ALKALI SIDE
SAMPLE B

FIG. 11
STRONGLY IONIZED
WEAKLY IONIZED
VERTICAL AXIS: RELATIVE INTENSITY WHEN STRONGEST SIGNAL
INTENSITY ($[M+2H]^{2+}$) IS ASSUMED TO BE 100%
HORIZONTAL AXIS

FIG. 12
VERTICAL AXIS: RELATIVE INTENSITY WHEN STRONGEST SIGNAL INTENSITY (QTALVLLK) IS ASSUMED TO BE 100%
HORIZONTAL AXIS: RETENTION TIME (MINUTE)

FIG. 13
ABSORBANCE
CONCENTRATION OF PORCINE SERUM ALBUMIN

Figure 14:
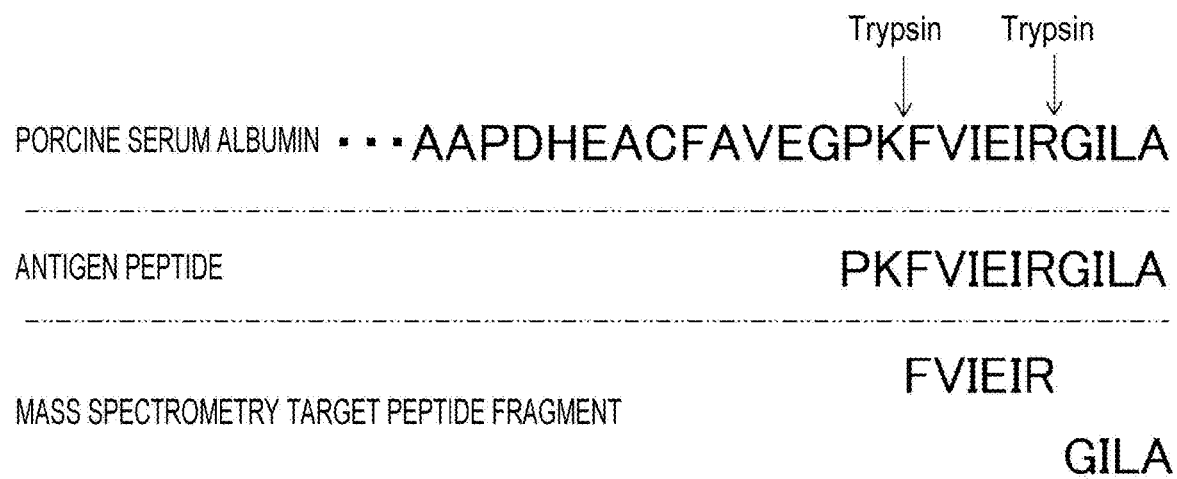
FIG. 14 is a diagram illustrating an amino acid sequence on a C-terminal side of a porcine serum albumin indicating a cleavage site by trypsin (upper row), an amino acid sequence of an antigen peptide (middle row), and an amino acid sequence of a mass spectrometry target peptide fragment generated by enzymatically digesting a porcine serum albumin standard solution with trypsin (lower row).

FIG. 14
PORCINE SERUM ALBUMIN
ANTIGEN PEPTIDE
MASS SPECTROMETRY TARGET PEPTIDE FRAGMENT

FIG. 15
GILA PEPTIDE CALIBRATION CURVE
AREA VALUE
PORCINE SERUM ALBUMIN

FIG. 16
FVIEIR PEPTIDE CALIBRATION CURVE
AREA VALUE
PORCINE SERUM ALBUMIN

The invention claimed is:

1. A method for detecting a specific protein in a sample, comprising:
  a protein digestion step of digesting the specific protein in one aliquot the sample into peptide fragments by a protease;
  a mass spectrometry step of detecting the peptide fragments from the one aliquot of the sample digested in the protein digestion step by mass spectrometry; and
  an immunoassay step of detecting the peptide fragments by immunoassay using an anti-peptide antibody specifically bonded to the specific protein from another aliquot of the sample;
  wherein both an amino acid sequence constituting a partial peptide of the specific protein used as an antigen for producing the anti-peptide antibody and an amino acid sequence constituting one of the peptide fragments detected in the mass spectrometry step have the same sequence and contain at least four amino acid residues.

2. The method according to claim 1, wherein the amino acid sequence constituting the partial peptide of the specific protein used as the antigen for producing the anti-peptide antibody and
  the amino acid sequence constituting the one of the peptide fragments corresponding to a signal detected with an intensity of 50% or more of a signal detected with the highest intensity in a case where mass spectrometry is performed using a peptide solution obtained by treating the specific protein with a proteolytic enzyme as a sample have the same sequence and contain at least four amino acid residues.

3. The method according to claim 1, wherein the one of the peptide fragments of the specific protein detected in the mass spectrometry step has the same amino acid sequence as at least a part of an amino acid sequence specifically recognized by the anti-peptide antibody.

4. The method according to claim 1, wherein the immunoassay performs an antigen-antibody reaction in the presence of an ionic surfactant.

5. The method according to claim 1, comprising an extraction step to treat a sample with an ionic surfactant in order to obtain a protein solution, wherein
  in the immunoassay step, the specific protein contained in the protein solution is detected, and
  in the mass spectrometry step, the one of the peptide fragments of the specific protein is detected using a peptide solution obtained by treating the protein solution or a treated product thereof with a proteolytic enzyme as a sample.

6. The method according to claim 1, wherein a standard solution is used as an analytical standard, wherein the standard solution contains a standard peptide, and wherein the standard peptide is a partial peptide of the specific protein, and contains at least a part of an amino acid sequence constituting the one of the peptide fragments detected in the mass spectrometry step, and to which the anti-peptide antibody can be bonded.

7. The method according to claim 6, wherein the standard solution used in the immunoassay step and the standard solution used in the mass spectrometry step include the same standard peptide.

8. The method according to claim 1, wherein the mass spectrometry step is performed after the immunoassay step in a case where a result of the immunoassay step is positive.

9. The method according to claim 1, wherein the mass spectrometry step is performed after the immunoassay step where a result of the immunoassay step is indeterminate as to being positive or negative.

10. The method according to claim 1, wherein the mass spectrometry step is performed in a case where a result of the immunoassay step is negative.

11. The method according to claim 1, wherein an ion derived from the one of the peptide fragments of the specific protein is selectively detected in the mass spectrometry step.

12. The method according to claim 1, wherein the one of the peptide fragments detected in the mass spectrometry step corresponds to a signal detected with an intensity of 50% or more of a signal detected with the highest intensity in a case where mass spectrometry is performed using a peptide solution obtained by treating the specific protein with a proteolytic enzyme as a sample.

13. The method according to claim 1, wherein the sample is a food sample.

14. The method according to claim 1, wherein the specific protein is an allergen protein.

15. The method according to claim 1, which is an immunoassay of a specific protein in a proteome and has the following characteristics:
  (1) a separation step of separating a protein in a sample is included;
  (2) in the mass spectrometry step, a protein separated in the separation step is identified by mass spectrometry; and
  (3) in the immunoassay step, a protein separated in the separation step and contained in the sample is measured by immunoassay using an anti-peptide antibody specifically bonded to the separated protein.

16. The method according to claim 15, comprising the following steps for producing the anti-peptide antibody after the mass spectrometry step:

(A) a selection step of selecting an amino acid sequence containing four or more amino acid residues with high specificity among amino acid sequences constituting a protein separated in the separation step;

(B) a peptide synthesis step of synthesizing a partial peptide containing an amino acid sequence selected in the selection step; and (C) an antibody production step of producing the anti-peptide antibody using the partial peptide as an antigen.

17. The method according to claim 15, wherein the mass spectrometry step is performed using a peptide solution obtained by treating a protein separated in the separation step with a proteolytic enzyme as a sample, and an anti-peptide antibody having, as an antigen, a partial peptide of the protein separated in the separation step, the partial peptide having at least four amino acid residues the same as those of an amino acid sequence constituting one or more kinds of peptide fragments corresponding to a signal detected with an intensity of 50% or more of a signal detected with the highest intensity in the mass spectrometry step, is used in the immunoassay step.

18. The method according to claim 15, wherein the separation step is performed by two-dimensional electrophoresis.

* * * * *

SEQUENCE LISTING

<160> NUMBER OF SEQ ID NOS: 61

<210> SEQ ID NO 1
<211> LENGTH: 607
<212> TYPE: PRT
<213> ORGANISM: Sus scrofa

<400> SEQUENCE: 1

```
Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Glu Pro Glu Arg Asn Glu Cys Phe Leu Gln
        115                 120                 125

His Lys Asn Asp Asn Pro Asp Ile Pro Lys Leu Lys Pro Asp Pro Val
    130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205

Arg Glu Lys Val Leu Thr Ser Ala Ala Lys Gln Arg Leu Lys Cys Ala
    210                 215                 220

Ser Ile Gln Lys Phe Gly Glu Arg Ala Phe Lys Ala Trp Ser Leu Ala
225                 230                 235                 240

Arg Leu Ser Gln Arg Phe Pro Lys Ala Asp Phe Thr Glu Ile Ser Lys
                245                 250                 255

Ile Val Thr Asp Leu Ala Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Thr Ile Ser Thr Lys Leu Lys Glu Cys Cys Asp Lys
    290                 295                 300

Pro Leu Leu Glu Lys Ser His Cys Ile Ala Glu Ala Lys Arg Asp Glu
305                 310                 315                 320

Leu Pro Ala Asp Leu Asn Pro Leu Glu His Asp Phe Val Glu Asp Lys
                325                 330                 335

Glu Val Cys Lys Asn Tyr Lys Glu Ala Lys His Val Phe Leu Gly Thr
            340                 345                 350

Phe Leu Tyr Glu Tyr Ser Arg Arg His Pro Asp Tyr Ser Val Ser Leu
        355                 360                 365
```

```
Leu Leu Arg Ile Ala Lys Ile Tyr Glu Ala Thr Leu Glu Asp Cys Cys
    370                 375                 380

Ala Lys Glu Asp Pro Pro Ala Cys Tyr Ala Thr Val Phe Asp Lys Phe
385                 390                 395                 400

Gln Pro Leu Val Asp Glu Pro Lys Asn Leu Ile Lys Gln Asn Cys Glu
                405                 410                 415

Leu Phe Glu Lys Leu Gly Glu Tyr Gly Phe Gln Asn Ala Leu Ile Val
            420                 425                 430

Arg Tyr Thr Lys Lys Val Pro Gln Val Ser Thr Pro Thr Leu Val Glu
                435                 440                 445

Val Ala Arg Lys Leu Gly Leu Val Gly Ser Arg Cys Cys Lys Arg Pro
450                 455                 460

Glu Glu Glu Arg Leu Ser Cys Ala Glu Asp Tyr Leu Ser Leu Val Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Lys Pro Lys Glu Phe Val Glu Gly
            515                 520                 525

Thr Phe Thr Phe His Ala Asp Leu Cys Thr Leu Pro Glu Asp Glu Lys
            530                 535                 540

Gln Ile Lys Lys Gln Thr Ala Leu Val Glu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
                580                 585                 590

Val Glu Gly Pro Lys Phe Val Ile Glu Ile Arg Gly Ile Leu Ala
            595                 600                 605

<210> SEQ ID NO 2
<211> LENGTH: 17
<212> TYPE: PRT
<213> ORGANISM: Sus scrofa

<400> SEQUENCE: 2

Trp Val Thr Phe Ile Ser Leu Leu Phe Leu Phe Ser Ser Ala Tyr Ser
1               5                   10                  15

Arg

<210> SEQ ID NO 3
<211> LENGTH: 4
<212> TYPE: PRT
<213> ORGANISM: Sus scrofa

<400> SEQUENCE: 3

Gly Val Phe Arg
1

<210> SEQ ID NO 4
<211> LENGTH: 4
<212> TYPE: PRT
<213> ORGANISM: Sus scrofa

<400> SEQUENCE: 4

Asp Thr Tyr Lys
1
```

```
<210> SEQ ID NO 5
<211> LENGTH: 6
<212> TYPE: PRT
<213> ORGANISM: Sus scrofa

<400> SEQUENCE: 5

Ser Glu Ile Ala His Arg
1               5

<210> SEQ ID NO 6
<211> LENGTH: 8
<212> TYPE: PRT
<213> ORGANISM: Sus scrofa

<400> SEQUENCE: 6

Asp Leu Gly Glu Gln Tyr Phe Lys
1               5

<210> SEQ ID NO 7
<211> LENGTH: 21
<212> TYPE: PRT
<213> ORGANISM: Sus scrofa

<400> SEQUENCE: 7

Gly Leu Val Leu Ile Ala Phe Ser Gln His Leu Gln Gln Cys Pro Tyr
1               5                   10                  15

Glu Glu His Val Lys
            20

<210> SEQ ID NO 8
<211> LENGTH: 7
<212> TYPE: PRT
<213> ORGANISM: Sus scrofa

<400> SEQUENCE: 8

Glu Val Thr Glu Phe Ala Lys
1               5

<210> SEQ ID NO 9
<211> LENGTH: 13
<212> TYPE: PRT
<213> ORGANISM: Sus scrofa

<400> SEQUENCE: 9

Thr Cys Val Ala Asp Glu Ser Ala Glu Asn Cys Asp Lys
1               5                   10

<210> SEQ ID NO 10
<211> LENGTH: 9
<212> TYPE: PRT
<213> ORGANISM: Sus scrofa

<400> SEQUENCE: 10

Ser Ile His Thr Leu Phe Gly Asp Lys
1               5

<210> SEQ ID NO 11
<211> LENGTH: 8
<212> TYPE: PRT
<213> ORGANISM: Sus scrofa

<400> SEQUENCE: 11

Leu Cys Ala Ile Pro Ser Leu Arg
1               5
```

```
<210> SEQ ID NO 12
<211> LENGTH: 12
<212> TYPE: PRT
<213> ORGANISM: Sus scrofa

<400> SEQUENCE: 12

Glu His Tyr Gly Asp Leu Ala Asp Cys Cys Glu Lys
1               5                   10

<210> SEQ ID NO 13
<211> LENGTH: 5
<212> TYPE: PRT
<213> ORGANISM: Sus scrofa

<400> SEQUENCE: 13

Glu Glu Pro Glu Arg
1               5

<210> SEQ ID NO 14
<211> LENGTH: 8
<212> TYPE: PRT
<213> ORGANISM: Sus scrofa

<400> SEQUENCE: 14

Asn Glu Cys Phe Leu Gln His Lys
1               5

<210> SEQ ID NO 15
<211> LENGTH: 8
<212> TYPE: PRT
<213> ORGANISM: Sus scrofa

<400> SEQUENCE: 15

Asn Asp Asn Pro Asp Ile Pro Lys
1               5

<210> SEQ ID NO 16
<211> LENGTH: 16
<212> TYPE: PRT
<213> ORGANISM: Sus scrofa

<400> SEQUENCE: 16

Pro Asp Pro Val Ala Leu Cys Ala Asp Phe Gln Glu Asp Glu Gln Lys
1               5                   10                  15

<210> SEQ ID NO 17
<211> LENGTH: 4
<212> TYPE: PRT
<213> ORGANISM: Sus scrofa

<400> SEQUENCE: 17

Phe Trp Gly Lys
1

<210> SEQ ID NO 18
<211> LENGTH: 7
<212> TYPE: PRT
<213> ORGANISM: Sus scrofa

<400> SEQUENCE: 18

Tyr Leu Tyr Glu Ile Ala Arg
1               5
```

```
<210> SEQ ID NO 19
<211> LENGTH: 17
<212> TYPE: PRT
<213> ORGANISM: Sus scrofa

<400> SEQUENCE: 19

His Pro Tyr Phe Tyr Ala Pro Glu Leu Leu Tyr Tyr Ala Ile Ile Tyr
1               5                   10                  15

Lys

<210> SEQ ID NO 20
<211> LENGTH: 12
<212> TYPE: PRT
<213> ORGANISM: Sus scrofa

<400> SEQUENCE: 20

Asp Val Phe Ser Glu Cys Cys Gln Ala Ala Asp Lys
1               5                   10

<210> SEQ ID NO 21
<211> LENGTH: 7
<212> TYPE: PRT
<213> ORGANISM: Sus scrofa

<400> SEQUENCE: 21

Ala Ala Cys Leu Leu Pro Lys
1               5

<210> SEQ ID NO 22
<211> LENGTH: 5
<212> TYPE: PRT
<213> ORGANISM: Sus scrofa

<400> SEQUENCE: 22

Ile Glu His Leu Arg
1               5

<210> SEQ ID NO 23
<211> LENGTH: 7
<212> TYPE: PRT
<213> ORGANISM: Sus scrofa

<400> SEQUENCE: 23

Val Leu Thr Ser Ala Ala Lys
1               5

<210> SEQ ID NO 24
<211> LENGTH: 6
<212> TYPE: PRT
<213> ORGANISM: Sus scrofa

<400> SEQUENCE: 24

Cys Ala Ser Ile Gln Lys
1               5

<210> SEQ ID NO 25
<211> LENGTH: 4
<212> TYPE: PRT
<213> ORGANISM: Sus scrofa

<400> SEQUENCE: 25

Phe Gly Glu Arg
1
```

```
<210> SEQ ID NO 26
<211> LENGTH: 6
<212> TYPE: PRT
<213> ORGANISM: Sus scrofa

<400> SEQUENCE: 26

Ala Trp Ser Leu Ala Arg
1               5

<210> SEQ ID NO 27
<211> LENGTH: 4
<212> TYPE: PRT
<213> ORGANISM: Sus scrofa

<400> SEQUENCE: 27

Leu Ser Gln Arg
1

<210> SEQ ID NO 28
<211> LENGTH: 8
<212> TYPE: PRT
<213> ORGANISM: Sus scrofa

<400> SEQUENCE: 28

Ala Asp Phe Thr Glu Ile Ser Lys
1               5

<210> SEQ ID NO 29
<211> LENGTH: 7
<212> TYPE: PRT
<213> ORGANISM: Sus scrofa

<400> SEQUENCE: 29

Ile Val Thr Asp Leu Ala Lys
1               5

<210> SEQ ID NO 30
<211> LENGTH: 14
<212> TYPE: PRT
<213> ORGANISM: Sus scrofa

<400> SEQUENCE: 30

Glu Cys Cys His Gly Asp Leu Leu Glu Cys Ala Asp Asp Arg
1               5                   10

<210> SEQ ID NO 31
<211> LENGTH: 5
<212> TYPE: PRT
<213> ORGANISM: Sus scrofa

<400> SEQUENCE: 31

Ala Asp Leu Ala Lys
1               5

<210> SEQ ID NO 32
<211> LENGTH: 12
<212> TYPE: PRT
<213> ORGANISM: Sus scrofa

<400> SEQUENCE: 32

Tyr Ile Cys Glu Asn Gln Asp Thr Ile Ser Thr Lys
1               5                   10
```

```
<210> SEQ ID NO 33
<211> LENGTH: 5
<212> TYPE: PRT
<213> ORGANISM: Sus scrofa

<400> SEQUENCE: 33

Glu Cys Cys Asp Lys
1               5

<210> SEQ ID NO 34
<211> LENGTH: 5
<212> TYPE: PRT
<213> ORGANISM: Sus scrofa

<400> SEQUENCE: 34

Pro Leu Leu Glu Lys
1               5

<210> SEQ ID NO 35
<211> LENGTH: 8
<212> TYPE: PRT
<213> ORGANISM: Sus scrofa

<400> SEQUENCE: 35

Ser His Cys Ile Ala Glu Ala Lys
1               5

<210> SEQ ID NO 36
<211> LENGTH: 18
<212> TYPE: PRT
<213> ORGANISM: Sus scrofa

<400> SEQUENCE: 36

Asp Glu Leu Pro Ala Asp Leu Asn Pro Leu Glu His Asp Phe Val Glu
1               5                   10                  15

Asp Lys

<210> SEQ ID NO 37
<211> LENGTH: 4
<212> TYPE: PRT
<213> ORGANISM: Sus scrofa

<400> SEQUENCE: 37

Glu Val Cys Lys
1

<210> SEQ ID NO 38
<211> LENGTH: 13
<212> TYPE: PRT
<213> ORGANISM: Sus scrofa

<400> SEQUENCE: 38

His Val Phe Leu Gly Thr Phe Leu Tyr Glu Tyr Ser Arg
1               5                   10

<210> SEQ ID NO 39
<211> LENGTH: 11
<212> TYPE: PRT
<213> ORGANISM: Sus scrofa

<400> SEQUENCE: 39

His Pro Asp Tyr Ser Val Ser Leu Leu Leu Arg
1               5                   10
```

```
<210> SEQ ID NO 40
<211> LENGTH: 12
<212> TYPE: PRT
<213> ORGANISM: Sus scrofa

<400> SEQUENCE: 40

Ile Tyr Glu Ala Thr Leu Glu Asp Cys Cys Ala Lys
1               5                   10

<210> SEQ ID NO 41
<211> LENGTH: 13
<212> TYPE: PRT
<213> ORGANISM: Sus scrofa

<400> SEQUENCE: 41

Glu Asp Pro Pro Ala Cys Tyr Ala Thr Val Phe Asp Lys
1               5                   10

<210> SEQ ID NO 42
<211> LENGTH: 9
<212> TYPE: PRT
<213> ORGANISM: Sus scrofa

<400> SEQUENCE: 42

Phe Gln Pro Leu Val Asp Glu Pro Lys
1               5

<210> SEQ ID NO 43
<211> LENGTH: 4
<212> TYPE: PRT
<213> ORGANISM: Sus scrofa

<400> SEQUENCE: 43

Asn Leu Ile Lys
1

<210> SEQ ID NO 44
<211> LENGTH: 8
<212> TYPE: PRT
<213> ORGANISM: Sus scrofa

<400> SEQUENCE: 44

Gln Asn Cys Glu Leu Phe Glu Lys
1               5

<210> SEQ ID NO 45
<211> LENGTH: 13
<212> TYPE: PRT
<213> ORGANISM: Sus scrofa

<400> SEQUENCE: 45

Leu Gly Glu Tyr Gly Phe Gln Asn Ala Leu Ile Val Arg
1               5                   10

<210> SEQ ID NO 46
<211> LENGTH: 14
<212> TYPE: PRT
<213> ORGANISM: Sus scrofa

<400> SEQUENCE: 46

Val Pro Gln Val Ser Thr Pro Thr Leu Val Glu Val Ala Arg
1               5                   10
```

```
<210> SEQ ID NO 47
<211> LENGTH: 7
<212> TYPE: PRT
<213> ORGANISM: Sus scrofa

<400> SEQUENCE: 47

Leu Gly Leu Val Gly Ser Arg
1               5

<210> SEQ ID NO 48
<211> LENGTH: 5
<212> TYPE: PRT
<213> ORGANISM: Sus scrofa

<400> SEQUENCE: 48

Pro Glu Glu Glu Arg
1               5

<210> SEQ ID NO 49
<211> LENGTH: 14
<212> TYPE: PRT
<213> ORGANISM: Sus scrofa

<400> SEQUENCE: 49

Leu Ser Cys Ala Glu Asp Tyr Leu Ser Leu Val Leu Asn Arg
1               5                   10

<210> SEQ ID NO 50
<211> LENGTH: 7
<212> TYPE: PRT
<213> ORGANISM: Sus scrofa

<400> SEQUENCE: 50

Leu Cys Val Leu His Glu Lys
1               5

<210> SEQ ID NO 51
<211> LENGTH: 6
<212> TYPE: PRT
<213> ORGANISM: Sus scrofa

<400> SEQUENCE: 51

Thr Pro Val Ser Glu Lys
1               5

<210> SEQ ID NO 52
<211> LENGTH: 9
<212> TYPE: PRT
<213> ORGANISM: Sus scrofa

<400> SEQUENCE: 52

Cys Cys Thr Glu Ser Leu Val Asn Arg
1               5

<210> SEQ ID NO 53
<211> LENGTH: 13
<212> TYPE: PRT
<213> ORGANISM: Sus scrofa

<400> SEQUENCE: 53

Pro Cys Phe Ser Ala Leu Thr Pro Asp Glu Thr Tyr Lys
1               5                   10
```

```
<210> SEQ ID NO 54
<211> LENGTH: 21
<212> TYPE: PRT
<213> ORGANISM: Sus scrofa

<400> SEQUENCE: 54

Glu Phe Val Glu Gly Thr Phe Thr Phe His Ala Asp Leu Cys Thr Leu
1               5                   10                  15

Pro Glu Asp Glu Lys
            20

<210> SEQ ID NO 55
<211> LENGTH: 9
<212> TYPE: PRT
<213> ORGANISM: Sus scrofa

<400> SEQUENCE: 55

Gln Thr Ala Leu Val Glu Leu Leu Lys
1               5

<210> SEQ ID NO 56
<211> LENGTH: 9
<212> TYPE: PRT
<213> ORGANISM: Sus scrofa

<400> SEQUENCE: 56

Pro His Ala Thr Glu Glu Gln Leu Arg
1               5

<210> SEQ ID NO 57
<211> LENGTH: 12
<212> TYPE: PRT
<213> ORGANISM: Sus scrofa

<400> SEQUENCE: 57

Thr Val Leu Gly Asn Phe Ala Ala Phe Val Gln Lys
1               5                   10

<210> SEQ ID NO 58
<211> LENGTH: 17
<212> TYPE: PRT
<213> ORGANISM: Sus scrofa

<400> SEQUENCE: 58

Cys Cys Ala Ala Pro Asp His Glu Ala Cys Phe Ala Val Glu Gly Pro
1               5                   10                  15

Lys

<210> SEQ ID NO 59
<211> LENGTH: 6
<212> TYPE: PRT
<213> ORGANISM: Sus scrofa

<400> SEQUENCE: 59

Phe Val Ile Glu Ile Arg
1               5

<210> SEQ ID NO 60
<211> LENGTH: 4
<212> TYPE: PRT
<213> ORGANISM: Sus scrofa
```

-continued

```
<400> SEQUENCE: 60

Gly Ile Leu Ala
1

<210> SEQ ID NO 61
<211> LENGTH: 12
<212> TYPE: PRT
<213> ORGANISM: Sus scrofa

<400> SEQUENCE: 61

Pro Lys Phe Val Ile Glu Ile Arg Gly Ile Leu Ala
1               5                   10
```